(12) United States Patent
Avitable et al.

(10) Patent No.: US 10,751,221 B2
(45) Date of Patent: Aug. 25, 2020

(54) COMPRESSION SLEEVE WITH IMPROVED POSITION RETENTION

(75) Inventors: Raymond C. Avitable, Framingham, MA (US); Ross Kanter, Wrentham, MA (US); Del Brooks, Seneca, SC (US)

(73) Assignee: KPR U.S., LLC, Mansfield, MA (US)

( * ) Notice: Subject to any disclaimer, the term of this patent is extended or adjusted under 35 U.S.C. 154(b) by 218 days.

(21) Appl. No.: 12/881,245

(22) Filed: Sep. 14, 2010

(65) Prior Publication Data

US 2012/0065664 A1   Mar. 15, 2012

(51) Int. Cl.
*A61B 17/00* (2006.01)
*A61F 13/00* (2006.01)
(Continued)

(52) U.S. Cl.
CPC ........ *A61F 13/00995* (2013.01); *A61B 17/00* (2013.01); *A61B 17/12* (2013.01); *A61F 13/06* (2013.01); *A61F 13/085* (2013.01); *A61H 9/0078* (2013.01); *A61H 9/0092* (2013.01); *A61F 2013/00174* (2013.01); *A61H 2201/1697* (2013.01)

(58) Field of Classification Search
CPC ............... A61B 17/00; A61B 17/12; A61B 2017/12004; A61B 17/132; A61B 17/1322; A61B 17/1325; A61B 17/1327; A61B 17/135; A61B 17/1355; A61B 5/02; A61B 5/022; A61B 5/02233; A61F 5/30; A61F 5/34; A61F 5/32; A61F 2013/0028; A61F 2013/00468; A61F 13/06; A61F 13/061; A61F 5/0111; A61F 13/08; A61F 5/01; A61F 5/0102; A61F 5/0106; A61F 5/0109; A61F 5/012; A61F 5/0123; A61F 2005/0176; A61H 9/005; A61H 9/0078; A61H 9/0085; A61H 9/0092; A61H 2209/00
See application file for complete search history.

(56) References Cited

U.S. PATENT DOCUMENTS 908,959 A   1/1909   Cooke
910,689 A   1/1909   Kelly et al.
(Continued)

FOREIGN PATENT DOCUMENTS

CA   2582678 A1   4/2006
CN   1009155 A    1/1987
(Continued)

OTHER PUBLICATIONS

Mittelman, Jonathan S., MD: "Effectiveness of Leg Compression in Preventing Venous Stasis", The American Journal of Surgery, Dec. 1982, p. 611-613, vol. 144, No. 6, Elsevier Publ., Bridgewater, NJ, USA.
(Continued)

*Primary Examiner* — Darwin P Erezo
*Assistant Examiner* — Erin L Colello
(74) *Attorney, Agent, or Firm* — Arent Fox LLP

(57) ABSTRACT

A compression garment having first and second sections includes a stay up device for supporting the compression garment in position on the body. The stay up device is constructed to operatively engage a portion of the body to positively locate the stay up device, and thereby the garment relative to the body.

23 Claims, 13 Drawing Sheets

(51) Int. Cl.
  *A61F 13/06* (2006.01)
  *A61F 13/08* (2006.01)
  *A61H 9/00* (2006.01)
  *A61B 17/12* (2006.01)

(56) References Cited

U.S. PATENT DOCUMENTS

| | | | |
|---|---|---|---|
| 1,510,482 A | 10/1924 | Kramer | |
| 1,608,239 A | 11/1926 | Rosett | |
| 2,199,408 A | 5/1940 | La Liberte | |
| 2,250,617 A | 7/1941 | Argentin | |
| 2,489,388 A | 11/1949 | Rubin | |
| 2,533,504 A | 12/1950 | Poor | |
| 2,638,915 A | 5/1953 | Mitchell | |
| 2,676,587 A | 4/1954 | Corcoran | |
| 2,694,395 A | 11/1954 | Brown | |
| 2,853,998 A | 9/1958 | Emerson | |
| 2,880,721 A | 4/1959 | Corcoran | |
| 2,896,612 A | 7/1959 | Bates et al. | |
| 2,998,817 A | 9/1961 | Armstrong | |
| 3,164,152 A | 1/1965 | Vere Nicoll | |
| 3,245,405 A | 4/1966 | Gardner | |
| 3,288,132 A | 11/1966 | Meredith | |
| 3,351,055 A | 11/1967 | Gottfried | |
| 3,454,010 A | 7/1969 | Lilligren et al. | |
| 3,469,769 A | 9/1969 | Guenther | |
| 3,473,527 A | 10/1969 | Spiro | |
| 3,504,675 A * | 4/1970 | Bishop, Jr. | A61B 17/1322 606/202 |
| 3,561,435 A | 2/1971 | Nicholson | |
| 3,568,227 A | 3/1971 | Dunham | |
| 3,606,880 A | 9/1971 | Ogle, Jr. | |
| 3,638,334 A | 2/1972 | Malikowski | |
| 3,701,173 A | 10/1972 | Whitney | |
| 3,728,875 A | 4/1973 | Hartigan et al. | |
| 3,760,795 A | 9/1973 | Adelhed | |
| 3,770,040 A | 11/1973 | De Cicco | |
| 3,771,519 A | 11/1973 | Haake | |
| 3,786,805 A | 1/1974 | Tourin | |
| 3,824,992 A | 7/1974 | Nicholson et al. | |
| 3,826,249 A | 7/1974 | Lee et al. | |
| 3,862,629 A | 1/1975 | Rotta | |
| 3,868,952 A | 3/1975 | Hatton | |
| 3,877,426 A | 4/1975 | Nirschl | |
| 3,878,839 A | 4/1975 | Norton et al. | |
| 3,899,210 A | 8/1975 | Samhammer et al. | |
| 3,901,221 A | 8/1975 | Nicholson et al. | |
| 3,906,937 A | 9/1975 | Aronson | |
| 3,920,006 A | 11/1975 | Lapidus | |
| D239,981 S | 5/1976 | Arbuck et al. | |
| 3,955,565 A | 5/1976 | Johnson, Jr. | |
| 4,013,069 A | 3/1977 | Hasty | |
| 4,029,087 A | 6/1977 | Dye et al. | |
| 4,030,488 A | 6/1977 | Hasty | |
| 4,054,129 A | 10/1977 | Byars et al. | |
| 4,066,084 A | 1/1978 | Tillander | |
| 4,076,022 A | 2/1978 | Walker | |
| 4,091,804 A | 5/1978 | Hasty | |
| 4,116,236 A * | 9/1978 | Albert | A41D 13/065 2/24 |
| 4,146,021 A | 3/1979 | Brosseau et al. | |
| 4,149,529 A | 4/1979 | Copeland et al. | |
| 4,149,541 A | 4/1979 | Gammons et al. | |
| 4,153,050 A | 5/1979 | Bishop et al. | |
| 4,156,425 A | 5/1979 | Arkans | |
| 4,197,837 A | 4/1980 | Tringali et al. | |
| 4,198,961 A | 4/1980 | Arkans | |
| 4,201,203 A * | 5/1980 | Applegate | 602/26 |
| 4,202,312 A | 5/1980 | Mori et al. | |
| 4,202,325 A | 5/1980 | Villari et al. | |
| 4,206,751 A | 6/1980 | Schneider | |
| 4,207,875 A | 6/1980 | Arkans | |
| 4,207,876 A | 6/1980 | Annis | |
| 4,219,892 A | 9/1980 | Rigdon | |
| 4,253,449 A | 3/1981 | Arkans et al. | |
| D259,058 S * | 4/1981 | Marshall | D24/190 |
| 4,267,611 A | 5/1981 | Agulnick | |
| 4,270,527 A | 6/1981 | Peters et al. | |
| 4,280,485 A | 7/1981 | Arkans | |
| 4,294,238 A | 10/1981 | Woodford | |
| 4,294,240 A | 10/1981 | Thill | |
| 4,300,245 A | 11/1981 | Saunders | |
| 4,308,862 A | 1/1982 | Kalmar | |
| 4,311,135 A | 1/1982 | Brueckner et al. | |
| 4,320,746 A | 3/1982 | Arkans et al. | |
| 4,343,302 A | 8/1982 | Dillon | |
| 4,352,253 A | 10/1982 | Oswalt | |
| 4,355,632 A | 10/1982 | Sandman | |
| 4,363,125 A | 12/1982 | Brewer et al. | |
| 4,372,297 A | 2/1983 | Perlin | |
| 4,375,217 A | 3/1983 | Arkans | |
| 4,379,217 A | 4/1983 | Youmans | |
| 4,402,312 A * | 9/1983 | Villari | A61H 9/0078 601/152 |
| 4,408,599 A | 10/1983 | Mummert | |
| 4,417,587 A | 11/1983 | Ichinomiya et al. | |
| 4,425,912 A * | 1/1984 | Harper | A61F 5/0109 2/24 |
| 4,437,269 A | 3/1984 | Shaw | |
| 4,442,834 A | 4/1984 | Tucker et al. | |
| 4,445,505 A | 5/1984 | Labour et al. | |
| 4,453,538 A | 6/1984 | Whitney | |
| 4,522,197 A | 6/1985 | Hasegawa | |
| 4,531,516 A | 7/1985 | Poole et al. | |
| 4,547,906 A | 10/1985 | Nishida et al. | |
| 4,547,919 A | 10/1985 | Wang | |
| 4,552,821 A | 11/1985 | Gibbard et al. | |
| 4,580,816 A | 4/1986 | Campbell et al. | |
| 4,583,255 A | 4/1986 | Mogaki et al. | |
| 4,593,692 A | 6/1986 | Flowers | |
| 4,597,384 A | 7/1986 | Whitney | |
| 4,614,180 A | 9/1986 | Gardner et al. | |
| 4,624,244 A | 11/1986 | Taheri | |
| 4,650,452 A | 3/1987 | Jensen | |
| 4,657,003 A | 4/1987 | Wirtz | |
| 4,682,588 A | 7/1987 | Curlee | |
| 4,696,289 A | 9/1987 | Gardner et al. | |
| 4,699,424 A | 10/1987 | Andres et al. | |
| 4,702,232 A | 10/1987 | Gardner et al. | |
| 4,703,750 A | 11/1987 | Sebastian et al. | |
| 4,706,658 A | 11/1987 | Cronin | |
| 4,722,332 A | 2/1988 | Saggers | |
| 4,730,606 A | 3/1988 | Leininger | |
| 4,753,649 A | 6/1988 | Pazdernik | |
| 4,762,121 A | 8/1988 | Shienfeld | |
| 4,773,397 A | 9/1988 | Wright et al. | |
| 4,805,620 A | 2/1989 | Meistrell | |
| 4,809,684 A | 3/1989 | Gardner et al. | |
| 4,827,912 A | 5/1989 | Carrington et al. | |
| 4,832,010 A | 5/1989 | Lerman | |
| RE32,939 E | 6/1989 | Gardner et al. | |
| RE32,940 E | 6/1989 | Gardner et al. | |
| 4,836,194 A | 6/1989 | Sebastian et al. | |
| 4,836,691 A | 6/1989 | Suzuki et al. | |
| D302,301 S | 7/1989 | Robinette-Lehman | |
| 4,846,189 A | 7/1989 | Sun | |
| 4,869,265 A | 9/1989 | McEwen | |
| 4,872,448 A * | 10/1989 | Johnson, Jr. | A41D 13/0568 128/DIG. 20 |
| 4,876,788 A | 10/1989 | Steer et al. | |
| 4,883,073 A | 11/1989 | Aziz | |
| 4,886,053 A | 12/1989 | Neal | |
| 4,898,160 A | 2/1990 | Brownlee | |
| 4,913,136 A | 4/1990 | Chong et al. | |
| 4,938,207 A | 7/1990 | Vargo | |
| 4,938,208 A | 7/1990 | Dye | |
| 4,938,226 A | 7/1990 | Danielsson et al. | |
| 4,945,571 A | 8/1990 | Calvert | |
| 4,947,834 A | 8/1990 | Kartheus et al. | |
| 4,957,105 A | 9/1990 | Kurth | |
| 4,960,115 A | 10/1990 | Ranciato | |
| 4,964,402 A | 10/1990 | Grim et al. | |
| 4,977,891 A | 12/1990 | Grim | |
| 4,979,953 A | 12/1990 | Spence | |

(56) References Cited

U.S. PATENT DOCUMENTS

| | | | |
|---|---|---|---|
| 4,986,263 A * | 1/1991 | Dickerson | A61F 5/0109 2/22 |
| 4,989,273 A | 2/1991 | Cromartie | |
| 4,997,452 A | 3/1991 | Kovach et al. | |
| 5,007,411 A | 4/1991 | Dye | |
| 5,014,681 A | 5/1991 | Neeman et al. | |
| 5,022,387 A | 6/1991 | Hasty | |
| 5,031,604 A | 7/1991 | Dye | |
| 5,048,536 A | 9/1991 | McEwen | |
| 5,052,377 A | 10/1991 | Frajdenrajch | |
| 5,062,414 A | 11/1991 | Grim | |
| 5,069,219 A | 12/1991 | Knoblich | |
| 5,071,415 A | 12/1991 | Takemoto | |
| 5,080,951 A | 1/1992 | Guthrie | |
| 5,082,284 A | 1/1992 | Reed | |
| 5,109,832 A | 5/1992 | Proctor et al. | |
| 5,117,812 A | 6/1992 | McWhorter | |
| 5,120,300 A | 6/1992 | Shaw | |
| 5,135,473 A | 8/1992 | Epler et al. | |
| 5,139,475 A | 8/1992 | Peters | |
| 5,139,476 A | 8/1992 | Peters | |
| 5,139,479 A | 8/1992 | Peters | |
| 5,146,932 A | 9/1992 | McCabe | |
| 5,156,629 A | 10/1992 | Shane et al. | |
| 5,158,541 A | 10/1992 | McCurley | |
| 5,168,576 A | 12/1992 | Krent et al. | |
| 5,172,689 A | 12/1992 | Wright | |
| D332,495 S | 1/1993 | Lake | |
| 5,179,941 A | 1/1993 | Siemssen et al. | |
| 5,181,522 A | 1/1993 | McEwen | |
| 5,186,163 A | 2/1993 | Dye | |
| 5,193,549 A | 3/1993 | Bellin et al. | |
| 5,211,162 A | 5/1993 | Gillen, Jr. et al. | |
| 5,226,245 A | 7/1993 | Lamont | |
| 5,228,478 A | 7/1993 | Kleisle | |
| 5,230,335 A | 7/1993 | Johnson, Jr. et al. | |
| 5,245,990 A | 9/1993 | Bertinin | |
| 5,259,397 A | 11/1993 | McCabe | |
| 5,261,871 A * | 11/1993 | Greenfield | 602/26 |
| 5,263,473 A | 11/1993 | McWhorter | |
| 5,275,588 A | 1/1994 | Matsumoto et al. | |
| 5,277,695 A | 1/1994 | Johnson, Jr. et al. | |
| 5,277,697 A | 1/1994 | France et al. | |
| 5,288,286 A | 2/1994 | Davis et al. | |
| 5,312,431 A | 5/1994 | McEwen | |
| 5,314,455 A | 5/1994 | Johnson, Jr. et al. | |
| 5,334,135 A | 8/1994 | Grim et al. | |
| 5,342,285 A | 8/1994 | Dye | |
| 5,354,260 A | 10/1994 | Cook | |
| 5,378,224 A | 1/1995 | Billotti | |
| 5,383,894 A | 1/1995 | Dye | |
| 5,383,919 A | 1/1995 | Kelly et al. | |
| 5,385,538 A | 1/1995 | Mann | |
| 5,389,065 A | 2/1995 | Johnson, Jr. | |
| 5,391,141 A | 2/1995 | Hamilton | |
| 5,399,153 A | 3/1995 | Caprio, Jr. et al. | |
| 5,403,265 A | 4/1995 | Berguer et al. | |
| 5,406,661 A | 4/1995 | Pekar | |
| 5,407,421 A | 4/1995 | Goldsmith | |
| D358,216 S | 5/1995 | Dye | |
| 5,411,037 A * | 5/1995 | Hess | A61F 5/0109 128/882 |
| 5,413,582 A | 5/1995 | Eaton | |
| 5,419,757 A | 5/1995 | Daneshvar | |
| 5,425,701 A | 6/1995 | Oster et al. | |
| 5,435,009 A | 7/1995 | Schild et al. | |
| 5,437,595 A | 8/1995 | Smith | |
| 5,437,610 A | 8/1995 | Cariapa et al. | |
| 5,441,533 A | 8/1995 | Johnson et al. | |
| 5,443,440 A | 8/1995 | Tumey et al. | |
| 5,449,341 A | 9/1995 | Harris | |
| 5,449,379 A | 9/1995 | Hadtke | |
| 5,450,858 A | 9/1995 | Zablotsky et al. | |
| 5,451,201 A | 9/1995 | Prengler | |
| 5,453,081 A | 9/1995 | Hansen | |
| 5,455,969 A | 10/1995 | Pratson et al. | |
| 5,458,265 A | 10/1995 | Hester et al. | |
| 5,462,517 A | 10/1995 | Mann | |
| 5,466,250 A | 11/1995 | Johnson, Jr. et al. | |
| 5,470,156 A | 11/1995 | May | |
| 5,478,119 A | 12/1995 | Dye | |
| 5,489,259 A | 2/1996 | Jacobs et al. | |
| 5,496,262 A | 3/1996 | Johnson, Jr. et al. | |
| 5,503,620 A | 4/1996 | Danzger | |
| 5,511,552 A | 4/1996 | Johnson | |
| 5,513,658 A | 5/1996 | Goseki | |
| 5,514,081 A | 5/1996 | Mann | |
| 5,514,155 A | 5/1996 | Daneshvar | |
| 5,527,267 A | 6/1996 | Billotti | |
| 5,554,105 A | 9/1996 | Taylor | |
| D376,013 S | 11/1996 | Sandman et al. | |
| 5,575,762 A | 11/1996 | Peeler et al. | |
| 5,578,055 A | 11/1996 | McEwen | |
| 5,584,798 A | 12/1996 | Fox | |
| 5,588,954 A | 12/1996 | Ribando et al. | |
| 5,588,955 A | 12/1996 | Johnson, Jr. et al. | |
| 5,588,956 A | 12/1996 | Billotti | |
| 5,591,200 A | 1/1997 | Cone et al. | |
| 5,591,337 A | 1/1997 | Lynn et al. | |
| 5,603,690 A | 2/1997 | Barry | |
| 5,609,570 A | 3/1997 | Lamont | |
| 5,620,411 A | 4/1997 | Schumann et al. | |
| 5,622,113 A | 4/1997 | Hansen | |
| 5,626,556 A | 5/1997 | Tobler et al. | |
| 5,626,557 A | 5/1997 | Mann | |
| 5,634,889 A | 6/1997 | Gardner et al. | |
| 5,637,106 A | 6/1997 | Mitchell et al. | |
| 5,640,714 A | 6/1997 | Tanaka | |
| 5,649,954 A | 7/1997 | McEwen | |
| 5,653,244 A | 8/1997 | Shaw | |
| D383,547 S | 9/1997 | Mason et al. | |
| 5,664,270 A | 9/1997 | Bell et al. | |
| 5,669,872 A | 9/1997 | Fox | |
| 5,673,028 A | 9/1997 | Levy | |
| 5,674,262 A | 10/1997 | Tumey | |
| 5,695,453 A | 12/1997 | Neal | |
| 5,704,999 A | 1/1998 | Lukich et al. | |
| 5,711,757 A | 1/1998 | Bryant | |
| 5,711,760 A | 1/1998 | Ibrahim | |
| 5,717,996 A | 2/1998 | Feldmann | |
| 5,728,055 A | 3/1998 | Sebastian | |
| 5,728,057 A | 3/1998 | Ouellette et al. | |
| 5,730,710 A | 3/1998 | Eichhorn et al. | |
| 5,733,304 A | 3/1998 | Spence | |
| 5,741,295 A | 4/1998 | McEwen | |
| 5,746,213 A | 5/1998 | Marks | |
| 5,759,167 A * | 6/1998 | Shields et al. | 602/26 |
| 5,765,298 A | 6/1998 | Potter et al. | |
| 5,769,800 A | 6/1998 | Gelfand et al. | |
| 5,769,801 A | 6/1998 | Tumey et al. | |
| 5,790,998 A | 8/1998 | Crescimbeni | |
| 5,795,312 A | 8/1998 | Dye | |
| 5,797,851 A | 8/1998 | Byrd | |
| 5,823,981 A * | 10/1998 | Grim | A61F 5/0109 602/13 |
| 5,833,639 A | 11/1998 | Nunes et al. | |
| 5,840,049 A | 11/1998 | Tumey et al. | |
| 5,843,007 A | 12/1998 | McEwen et al. | |
| D403,775 S | 1/1999 | Davis et al. | |
| D405,884 S | 2/1999 | Roper | |
| 5,876,359 A | 3/1999 | Bock et al. | |
| 5,891,065 A | 4/1999 | Cariapa et al. | |
| 5,894,682 A | 4/1999 | Broz | |
| D411,301 S | 6/1999 | Hampson et al. | |
| 5,916,183 A | 6/1999 | Reid | |
| 5,925,010 A | 7/1999 | Caprio, Jr. | |
| 5,926,850 A | 7/1999 | Han | |
| 5,938,628 A | 8/1999 | Oguri et al. | |
| 5,951,502 A | 9/1999 | Peeler et al. | |
| 5,957,872 A | 9/1999 | Flick | |
| 5,966,763 A | 10/1999 | Thomas et al. | |
| 5,968,072 A | 10/1999 | Hite et al. | |
| 5,970,519 A | 10/1999 | Weber | |
| 5,976,099 A | 11/1999 | Kellogg | |

(56) References Cited

U.S. PATENT DOCUMENTS

| | | |
|---|---|---|
| 5,976,300 A | 11/1999 | Buchanan et al. |
| 5,988,704 A | 11/1999 | Ryhman |
| 5,989,204 A | 11/1999 | Lina |
| 5,991,654 A | 11/1999 | Tumey et al. |
| 5,997,495 A | 12/1999 | Cook et al. |
| 5,997,981 A | 12/1999 | McCormack et al. |
| 6,001,119 A | 12/1999 | Hampson et al. |
| 6,007,559 A | 12/1999 | Arkans |
| 6,010,471 A | 1/2000 | Ben-Noon |
| 6,021,780 A | 2/2000 | Darby |
| 6,036,718 A | 3/2000 | Ledford et al. |
| 6,048,326 A | 4/2000 | Davis et al. |
| 6,051,016 A | 4/2000 | Mesaros et al. |
| 6,056,713 A | 5/2000 | Hayashi |
| 6,062,244 A | 5/2000 | Arkans |
| 6,066,217 A | 5/2000 | Dibble et al. |
| 6,076,193 A | 6/2000 | Hood |
| 6,080,120 A | 6/2000 | Sandman et al. |
| D428,153 S | 7/2000 | Davis |
| 6,110,135 A | 8/2000 | Madow et al. |
| 6,120,469 A | 9/2000 | Bruder |
| 6,126,683 A | 10/2000 | Momtaheni |
| 6,129,688 A | 10/2000 | Arkans |
| 6,129,695 A | 10/2000 | Peters et al. |
| 6,134,720 A | 10/2000 | Foreman |
| 6,135,116 A | 10/2000 | Vogel et al. |
| 6,145,143 A | 11/2000 | Hicks et al. |
| 6,149,600 A | 11/2000 | Poorman-Ketchum |
| 6,149,616 A * | 11/2000 | Szlema et al. .................. 602/26 |
| 6,152,495 A | 11/2000 | Hoffmann et al. |
| 6,152,893 A | 11/2000 | Pigg et al. |
| 6,168,539 B1 | 1/2001 | Maina |
| 6,171,271 B1 | 1/2001 | Hörnberg |
| 6,179,796 B1 | 1/2001 | Waldridge |
| 6,197,045 B1 | 3/2001 | Carson |
| 6,203,510 B1 * | 3/2001 | Takeuchi ............ A61H 9/0078 601/152 |
| 6,231,532 B1 | 3/2001 | Watson et al. |
| 6,209,159 B1 | 4/2001 | Murphy |
| 6,212,719 B1 | 4/2001 | Thomas et al. |
| 6,231,507 B1 | 5/2001 | Zikorus et al. |
| 6,245,023 B1 | 6/2001 | Clemmons |
| 6,254,554 B1 | 7/2001 | Turtzo |
| 6,257,626 B1 | 7/2001 | Campau |
| 6,257,627 B1 | 7/2001 | Fujiwara et al. |
| 6,260,201 B1 | 7/2001 | Rankin |
| 6,290,662 B1 | 9/2001 | Morris et al. |
| 6,290,664 B1 | 9/2001 | Nauert |
| 6,315,745 B1 | 11/2001 | Kloecker |
| 6,319,215 B1 | 11/2001 | Manor et al. |
| 6,322,530 B1 | 11/2001 | Johnson, Jr. et al. |
| 6,336,935 B1 | 1/2002 | Davis et al. |
| 6,338,723 B1 | 1/2002 | Carpenter et al. |
| 6,349,506 B1 | 2/2002 | Pace et al. |
| 6,358,219 B1 | 3/2002 | Arkans |
| 6,368,357 B1 | 4/2002 | Schon et al. |
| 6,375,633 B1 | 4/2002 | Endress et al. |
| 6,385,778 B1 | 5/2002 | Johnson |
| 6,385,864 B1 | 5/2002 | Sell, Jr. et al. |
| 6,387,065 B1 | 5/2002 | Tumey |
| 6,402,879 B1 | 6/2002 | Tawney et al. |
| 6,409,691 B1 | 6/2002 | Dakin et al. |
| 6,423,053 B1 | 7/2002 | Lee |
| 6,436,064 B1 | 8/2002 | Kloecker |
| 6,440,093 B1 | 8/2002 | McEwen et al. |
| 6,447,460 B1 | 9/2002 | Zheng et al. |
| 6,463,934 B1 | 10/2002 | Johnson, Jr. et al. |
| 6,468,237 B1 | 10/2002 | Lina |
| 6,478,757 B1 | 11/2002 | Barak |
| 6,478,761 B2 | 11/2002 | Bracamonte-Sommer |
| 6,488,643 B1 | 12/2002 | Tumey et al. |
| 6,494,852 B1 | 12/2002 | Barak et al. |
| 6,508,205 B1 | 1/2003 | Zink |
| 6,520,926 B2 | 2/2003 | Hall |
| 6,526,597 B1 | 3/2003 | Shepard |
| 6,527,727 B2 | 3/2003 | Itonaga et al. |
| 6,537,298 B2 | 3/2003 | Dedo |
| 6,540,707 B1 | 4/2003 | Stark et al. |
| 6,544,202 B2 | 4/2003 | McEwen et al. |
| 6,549,748 B2 | 4/2003 | Miura |
| 6,551,280 B1 | 4/2003 | Knighton et al. |
| 6,554,785 B1 | 4/2003 | Sroufe et al. |
| 6,557,704 B1 | 5/2003 | Randolph |
| 6,558,338 B1 | 5/2003 | Wasserman |
| 6,562,060 B1 | 5/2003 | Momtaheni |
| 6,589,267 B1 | 7/2003 | Hui |
| 6,589,534 B1 | 7/2003 | Shaul et al. |
| 6,592,534 B1 | 7/2003 | Rutt et al. |
| 6,593,508 B1 | 7/2003 | Harder |
| 6,598,249 B2 | 7/2003 | Pajanacci et al. |
| D478,995 S | 8/2003 | Cipra et al. |
| 6,616,622 B1 | 9/2003 | Barberio |
| 6,618,859 B1 | 9/2003 | Kadymir et al. |
| 6,629,941 B1 | 10/2003 | Ishibashi et al. |
| 6,645,165 B2 | 11/2003 | Waldridge et al. |
| D484,986 S | 1/2004 | Cipra et al. |
| 6,676,614 B1 | 1/2004 | Hansen et al. |
| 6,682,547 B2 | 1/2004 | McEwen et al. |
| 6,685,661 B2 | 2/2004 | Peled |
| 6,719,711 B1 | 4/2004 | Islava |
| 6,726,641 B2 | 4/2004 | Chiang et al. |
| 6,746,470 B2 | 6/2004 | McEwen et al. |
| 6,762,337 B2 | 7/2004 | Boukanov et al. |
| 6,762,338 B2 | 7/2004 | Harder |
| 6,842,915 B2 | 1/2005 | Turner et al. |
| 6,846,294 B2 | 1/2005 | Rastegar et al. |
| 6,846,295 B1 | 1/2005 | Ben-Nun |
| 6,849,057 B2 | 2/2005 | Satou et al. |
| 6,852,089 B2 | 2/2005 | Kloecker et al. |
| 6,860,862 B2 | 3/2005 | Waldridge et al. |
| 6,862,989 B2 | 3/2005 | Belanger et al. |
| 6,866,636 B2 | 3/2005 | Inoue et al. |
| 6,869,409 B2 | 3/2005 | Rothman et al. |
| D506,553 S | 6/2005 | Tesluk |
| 6,945,944 B2 | 9/2005 | Kuiper et al. |
| D510,626 S | 10/2005 | Krahner et al. |
| 6,973,690 B2 | 12/2005 | Muci et al. |
| 6,984,215 B2 | 1/2006 | Shah et al. |
| 6,991,613 B2 | 1/2006 | Sensabaugh |
| 7,011,640 B2 | 3/2006 | Patterson et al. |
| 7,022,096 B1 | 4/2006 | Alfieri |
| 7,041,074 B1 | 5/2006 | Averianov et al. |
| 7,044,924 B1 | 5/2006 | Roth et al. |
| 7,048,703 B2 | 5/2006 | Riach |
| 7,083,586 B2 * | 8/2006 | Simmons ............. A61F 5/0109 602/23 |
| 7,090,500 B1 | 8/2006 | Guttman |
| D533,668 S | 12/2006 | Brown |
| 7,166,077 B2 | 1/2007 | Millay et al. |
| 7,217,249 B2 | 5/2007 | Scott |
| D545,972 S | 7/2007 | Wierenga et al. |
| 7,237,272 B2 | 7/2007 | Botcher |
| 7,238,080 B2 | 7/2007 | Gimble |
| 7,258,676 B2 | 8/2007 | Calderon et al. |
| D550,367 S | 9/2007 | Nash |
| 7,276,037 B2 | 10/2007 | Ravikumar |
| 7,276,039 B2 | 10/2007 | Garelick et al. |
| 7,278,980 B1 | 10/2007 | Garelick et al. |
| 7,282,038 B2 | 10/2007 | Gillis et al. |
| 7,285,103 B2 | 10/2007 | Nathanson |
| 7,288,076 B2 | 10/2007 | Grim et al. |
| 7,297,128 B2 | 11/2007 | Binder et al. |
| 7,300,410 B1 | 11/2007 | Weber |
| 7,303,539 B2 | 12/2007 | Binder et al. |
| 7,306,568 B2 | 12/2007 | Diana |
| 7,310,847 B2 | 12/2007 | Bolkan et al. |
| 7,318,812 B2 | 1/2008 | Taylor et al. |
| D562,461 S | 2/2008 | Nash |
| D562,462 S | 2/2008 | Muir et al. |
| 7,326,227 B2 | 2/2008 | Dedo et al. |
| 7,329,232 B2 | 2/2008 | Lipshaw et al. |
| 7,351,217 B2 | 4/2008 | Scherpenborg |
| 7,353,770 B2 | 4/2008 | Sanguinetti |
| 7,354,410 B2 | 4/2008 | Perry et al. |

(56) References Cited

U.S. PATENT DOCUMENTS

| | | | |
|---|---|---|---|
| 7,354,411 B2 | 4/2008 | Perry et al. | |
| 7,374,550 B2 | 5/2008 | Hansen et al. | |
| D577,124 S | 9/2008 | Freeland et al. | |
| 7,424,936 B2 | 9/2008 | McClellan | |
| 7,442,175 B2 * | 10/2008 | Meyer | A61F 13/06 |
| | | | 601/151 |
| 7,465,283 B2 | 12/2008 | Grim et al. | |
| 7,468,048 B2 | 12/2008 | Meehan | |
| 7,473,816 B2 | 1/2009 | Hall | |
| D594,561 S | 6/2009 | Freeland et al. | |
| 7,543,399 B2 | 6/2009 | Kilgore et al. | |
| 7,559,908 B2 | 7/2009 | Ravikumar | |
| 7,578,799 B2 | 8/2009 | Thorsteinsson et al. | |
| 7,591,796 B1 | 9/2009 | Barak et al. | |
| 7,591,797 B2 | 9/2009 | Hakonson et al. | |
| 7,597,675 B2 | 10/2009 | Ingimundarson et al. | |
| 7,615,027 B2 | 11/2009 | Nordt, III et al. | |
| 7,618,389 B2 | 11/2009 | Nordt, III et al. | |
| 7,625,348 B2 | 12/2009 | Young et al. | |
| 7,637,879 B2 | 12/2009 | Barak et al. | |
| D608,006 S | 1/2010 | Avitable et al. | |
| 7,654,117 B2 | 2/2010 | Barnett | |
| 7,748,090 B2 | 7/2010 | Seth et al. | |
| 7,766,890 B2 | 8/2010 | Ito et al. | |
| 7,780,698 B2 * | 8/2010 | McEwen et al. | 606/203 |
| 7,803,358 B2 | 9/2010 | Gordan et al. | |
| 7,827,624 B1 | 11/2010 | Cole | |
| 8,177,734 B2 | 5/2012 | Vess | |
| 8,419,666 B2 | 4/2013 | Liu et al. | |
| 8,506,508 B2 * | 8/2013 | Avitable | A61H 9/0078 |
| | | | 156/73.5 |
| 2001/0018564 A1 | 8/2001 | Manor et al. | |
| 2002/0068886 A1 | 6/2002 | Lin | |
| 2002/0069731 A1 | 6/2002 | Soucy | |
| 2002/0115949 A1 | 8/2002 | Kuslich et al. | |
| 2002/0121235 A1 | 9/2002 | Carpenter et al. | |
| 2003/0018313 A1 | 1/2003 | Tanzer et al. | |
| 2003/0065357 A1 | 4/2003 | Dedo et al. | |
| 2003/0083605 A1 | 5/2003 | Edmund | |
| 2003/0130644 A1 | 7/2003 | Baker | |
| 2003/0191420 A1 * | 10/2003 | Kuiper et al. | 602/13 |
| 2003/0199922 A1 | 10/2003 | Buckman | |
| 2004/0010212 A1 | 1/2004 | Kuiper et al. | |
| 2004/0039317 A1 | 2/2004 | Souney et al. | |
| 2004/0039413 A1 | 2/2004 | Akerfeldt et al. | |
| 2004/0054306 A1 | 3/2004 | Roth et al. | |
| 2004/0068290 A1 | 4/2004 | Bates et al. | |
| 2004/0097860 A1 | 5/2004 | Tauber | |
| 2004/0158283 A1 | 8/2004 | Shook et al. | |
| 2004/0158285 A1 | 8/2004 | Pillai | |
| 2004/0176715 A1 | 9/2004 | Nelson | |
| 2004/0181156 A1 | 9/2004 | Kingsford et al. | |
| 2004/0181254 A1 | 9/2004 | Choi et al. | |
| 2004/0199090 A1 | 10/2004 | Sanders et al. | |
| 2004/0210167 A1 | 10/2004 | Webster | |
| 2004/0236258 A1 | 11/2004 | Burns et al. | |
| 2005/0070828 A1 | 3/2005 | Hampson et al. | |
| 2005/0154336 A1 | 7/2005 | Kloecker et al. | |
| 2005/0165340 A1 | 7/2005 | Dunn | |
| 2005/0187503 A1 * | 8/2005 | Tordella et al. | 602/13 |
| 2005/0209545 A1 | 9/2005 | Farrow et al. | |
| 2005/0242315 A1 | 11/2005 | Lund | |
| 2006/0010574 A1 | 1/2006 | Linnane et al. | |
| 2006/0020236 A1 | 1/2006 | Ben-Nun | |
| 2006/0026736 A1 * | 2/2006 | Nordt et al. | 2/125 |
| 2006/0089617 A1 | 4/2006 | Bunnelle | |
| 2006/0102423 A1 | 5/2006 | Lang et al. | |
| 2006/0135894 A1 | 6/2006 | Linnane et al. | |
| 2006/0137072 A1 | 6/2006 | Visco et al. | |
| 2006/0142719 A1 | 6/2006 | Vogt et al. | |
| 2006/0189907 A1 | 8/2006 | Pick et al. | |
| 2006/0211965 A1 | 9/2006 | Horn et al. | |
| 2006/0287672 A1 * | 12/2006 | McEwen et al. | 606/202 |
| 2006/0293151 A1 | 12/2006 | Rast | |
| 2007/0038167 A1 | 2/2007 | Tabron et al. | |
| 2007/0055188 A1 | 3/2007 | Avni et al. | |
| 2007/0088239 A1 | 4/2007 | Roth et al. | |
| 2007/0129658 A1 | 6/2007 | Hampson et al. | |
| 2007/0130732 A1 | 6/2007 | Matsumura et al. | |
| 2007/0135743 A1 | 6/2007 | Meyer | |
| 2007/0135835 A1 | 6/2007 | McEwen et al. | |
| 2007/0135836 A1 | 6/2007 | McEwen et al. | |
| 2007/0161933 A1 | 7/2007 | Ravikumar | |
| 2007/0167892 A1 | 7/2007 | Gramza et al. | |
| 2007/0167895 A1 | 7/2007 | Gramza et al. | |
| 2007/0179416 A1 | 8/2007 | Obrien et al. | |
| 2007/0197944 A1 | 8/2007 | Bruce et al. | |
| 2007/0219580 A1 | 9/2007 | McEwen et al. | |
| 2007/0244506 A1 | 10/2007 | McEwen et al. | |
| 2007/0260162 A1 | 11/2007 | Meyer et al. | |
| 2007/0261789 A1 | 11/2007 | Giori | |
| 2007/0264497 A1 | 11/2007 | Kong | |
| 2007/0276310 A1 | 11/2007 | Lipshaw et al. | |
| 2007/0276311 A1 | 11/2007 | Wieringa et al. | |
| 2007/0282233 A1 | 12/2007 | Meyer et al. | |
| 2008/0000477 A1 | 1/2008 | Huster et al. | |
| 2008/0004555 A1 | 1/2008 | Reis et al. | |
| 2008/0004560 A1 | 1/2008 | Miskie | |
| 2008/0021363 A1 | 1/2008 | Fee | |
| 2008/0023423 A1 | 1/2008 | Duffy | |
| 2008/0064996 A1 | 3/2008 | Bretl et al. | |
| 2008/0071202 A1 | 3/2008 | Nardi et al. | |
| 2008/0072629 A1 | 3/2008 | Gehring | |
| 2008/0086071 A1 | 4/2008 | Weatherly | |
| 2008/0087740 A1 | 4/2008 | Gusenoff et al. | |
| 2008/0103397 A1 | 5/2008 | Barak | |
| 2008/0103422 A1 | 5/2008 | Perry et al. | |
| 2008/0119771 A1 | 5/2008 | Jaccard | |
| 2008/0141428 A1 | 6/2008 | Kapah et al. | |
| 2008/0143007 A1 | 6/2008 | Tuma | |
| 2008/0183115 A1 | 7/2008 | Pierce | |
| 2008/0188786 A1 | 8/2008 | Hickling | |
| 2008/0208092 A1 | 8/2008 | Sawa | |
| 2008/0234615 A1 | 9/2008 | Cook et al. | |
| 2008/0243173 A1 | 10/2008 | Thorpe | |
| 2008/0245361 A1 | 10/2008 | Brown | |
| 2008/0249440 A1 | 10/2008 | Avitable et al. | |
| 2008/0249441 A1 | 10/2008 | Avitable et al. | |
| 2008/0249442 A1 | 10/2008 | Brown et al. | |
| 2008/0249443 A1 | 10/2008 | Avitable et al. | |
| 2008/0249444 A1 | 10/2008 | Avitable et al. | |
| 2008/0249447 A1 | 10/2008 | Brown et al. | |
| 2008/0249449 A1 | 10/2008 | Brown et al. | |
| 2008/0249455 A1 | 10/2008 | Brown et al. | |
| 2008/0249559 A1 * | 10/2008 | Brown et al. | 606/202 |
| 2008/0250551 A1 | 10/2008 | Mazzarolo | |
| 2008/0255485 A1 | 10/2008 | Johnson et al. | |
| 2008/0281351 A1 | 11/2008 | Croushorn et al. | |
| 2008/0300524 A1 * | 12/2008 | Scott | A61F 5/0106 |
| | | | 602/26 |
| 2008/0306420 A1 | 12/2008 | Vess | |
| 2008/0312682 A1 | 12/2008 | Shams et al. | |
| 2009/0005718 A1 | 1/2009 | Lightbourne | |
| 2009/0062703 A1 | 3/2009 | Meyer et al. | |
| 2009/0064919 A1 | 3/2009 | Greenwald | |
| 2009/0076432 A1 | 3/2009 | Winkler | |
| 2009/0082708 A1 | 3/2009 | Scott et al. | |
| 2009/0099562 A1 | 4/2009 | Ingimudarson et al. | |
| 2009/0110890 A1 | 4/2009 | Garza et al. | |
| 2009/0124944 A1 | 5/2009 | Ravikumar | |
| 2009/0133446 A1 | 5/2009 | Burrow et al. | |
| 2009/0137938 A1 | 5/2009 | Parivash | |
| 2009/0163842 A1 | 6/2009 | Cropper | |
| 2009/0171223 A1 | 7/2009 | McEwen et al. | |
| 2009/0177222 A1 | 7/2009 | Brown et al. | |
| 2009/0198160 A1 | 8/2009 | Coyne | |
| 2009/0198261 A1 | 8/2009 | Schweikert | |
| 2009/0227917 A1 | 9/2009 | Nardi | |
| 2009/0227919 A1 | 9/2009 | Nardi et al. | |
| 2009/0227922 A1 | 9/2009 | Nardi et al. | |
| 2009/0234265 A1 | 9/2009 | Reid et al. | |
| 2009/0270910 A1 | 10/2009 | Hargens et al. | |
| 2009/0278707 A1 | 11/2009 | Biggins et al. | |
| 2009/0281470 A1 | 11/2009 | Sandusky et al. | |

(56) References Cited

U.S. PATENT DOCUMENTS

| | | |
|---|---|---|
| 2009/0299249 A1 | 12/2009 | Wilkes et al. |
| 2009/0312681 A1 | 12/2009 | McSpadden et al. |
| 2009/0320174 A1 | 12/2009 | Turner |
| 2009/0326576 A1 | 12/2009 | Ben-Nun |
| 2010/0004575 A1 | 1/2010 | Vess |
| 2010/0004676 A1 | 1/2010 | McEwen et al. |
| 2010/0010408 A1 | 1/2010 | Linares |
| 2010/0016771 A1 | 1/2010 | Arbesman et al. |
| 2010/0022930 A1 | 1/2010 | Koby et al. |
| 2010/0037369 A1 | 2/2010 | Reichert |
| 2010/0042026 A1 | 2/2010 | Kloecker et al. |
| 2010/0042028 A1 | 2/2010 | Frank et al. |
| 2010/0081975 A1 | 4/2010 | Avitable et al. |
| 2010/0081977 A1 | 4/2010 | Vess |
| 2010/0210982 A1 | 8/2010 | Balachandran et al. |
| 2010/0268130 A1 | 10/2010 | Khan |
| 2012/0071801 A1 | 3/2012 | Avitable |
| 2012/0078146 A1 | 3/2012 | Deshpande |
| 2013/0310719 A1 | 11/2013 | Davis et al. |
| 2014/0236058 A1 | 8/2014 | Lee |

FOREIGN PATENT DOCUMENTS

| | | |
|---|---|---|
| DE | 1955539 A1 | 5/1971 |
| DE | 19846922 A1 | 4/2000 |
| EP | 0303029 A1 | 2/1989 |
| EP | 0408049 A2 | 1/1991 |
| EP | 0861651 A1 | 9/1998 |
| EP | 1468816 A1 | 10/2004 |
| EP | 2168554 A1 | 3/2010 |
| FR | 2813770 A1 | 3/2002 |
| GB | 2061086 A | 5/1981 |
| GB | 2178663 A | 2/1987 |
| GB | 2183483 A | 6/1987 |
| GB | 2313784 A | 12/1997 |
| GB | 2373444 A | 9/2002 |
| JP | 59218154 A | 12/1984 |
| JP | 60135110 U | 9/1985 |
| JP | 2002065782 | 3/2002 |
| JP | 2003310312 A | 11/2003 |
| JP | 2004081709 | 3/2004 |
| JP | 2005066247 | 3/2005 |
| JP | 2009000277 A | 1/2009 |
| WO | 9417765 A1 | 8/1994 |
| WO | 96/20685 A1 | 7/1996 |
| WO | 2005082315 A1 | 9/2005 |
| WO | 2006083865 A2 | 8/2006 |

OTHER PUBLICATIONS

Tyco Healthcare Kendall, SCD Response Catalog, Mar. 2000, pp. 1-2.

Tyco Healthcare Kendall, SCD Soft Sleeve Catalog, Apr. 2001, pp. 1-2.

The Kendall Company, Vascular Therapy Products Catalog, Jan. 1996, pp. 8-5 thru 8-7.

The Kendall Company, The New SCD Compression Sleeve, Aug. 1993, pp. 1-2.

Tyco Healthcare Kendall, Prevention Gets Personal Mar. 2001, pp. 1, 2, 4.

Kendall SCD, Sequential Compression Sleeves, Patent Information, Jan. 1993, 6 pages.

Chinese Office Action dated Aug. 27, 2013 regarding Chinese Application No. 201110269952.X, 7 pages.

English translation of Notice of Reasons for Rejection from corresponding Japanese Application No. 2011-191116 dated Jan. 29, 2013, 3 pgs.

Patent Examination Report No. 1 dated Apr. 4, 2013 in corresponding Australian Patent Application No. 2011213815, 7 pages.

Exam Report dated Apr. 17, 2013 in corresponding Canadian Patent Application No. 2,748,775, 2 pages.

Extended European Search Report dated Jun. 17, 2013 regarding European Application No. 11177787.6, 7 pgs.

Patent Examination Report No. 1 dated Aug. 22, 2014 in related Australian Patent Application serial No. 2013248259, 2 pages.

Office Action dated Jul. 29, 2014 in related Japanese Patent Application serial No. 2013-176584, 4 pages.

Office Action dated Sep. 6, 2015 in related Chinese Application No. 2014103673.X, 10 pages.

Office Action dated Dec. 15, 2015 in related European Patent Application No. 11177787.6, 3 pages.

Office Action dated May 5, 2016 in related Chinese Patent Application No. 201410361673.X, 13 pages.

Examination Report for European Patent application No. 11177787.6, dated Nov. 20, 2018, 5 pages.

\* cited by examiner

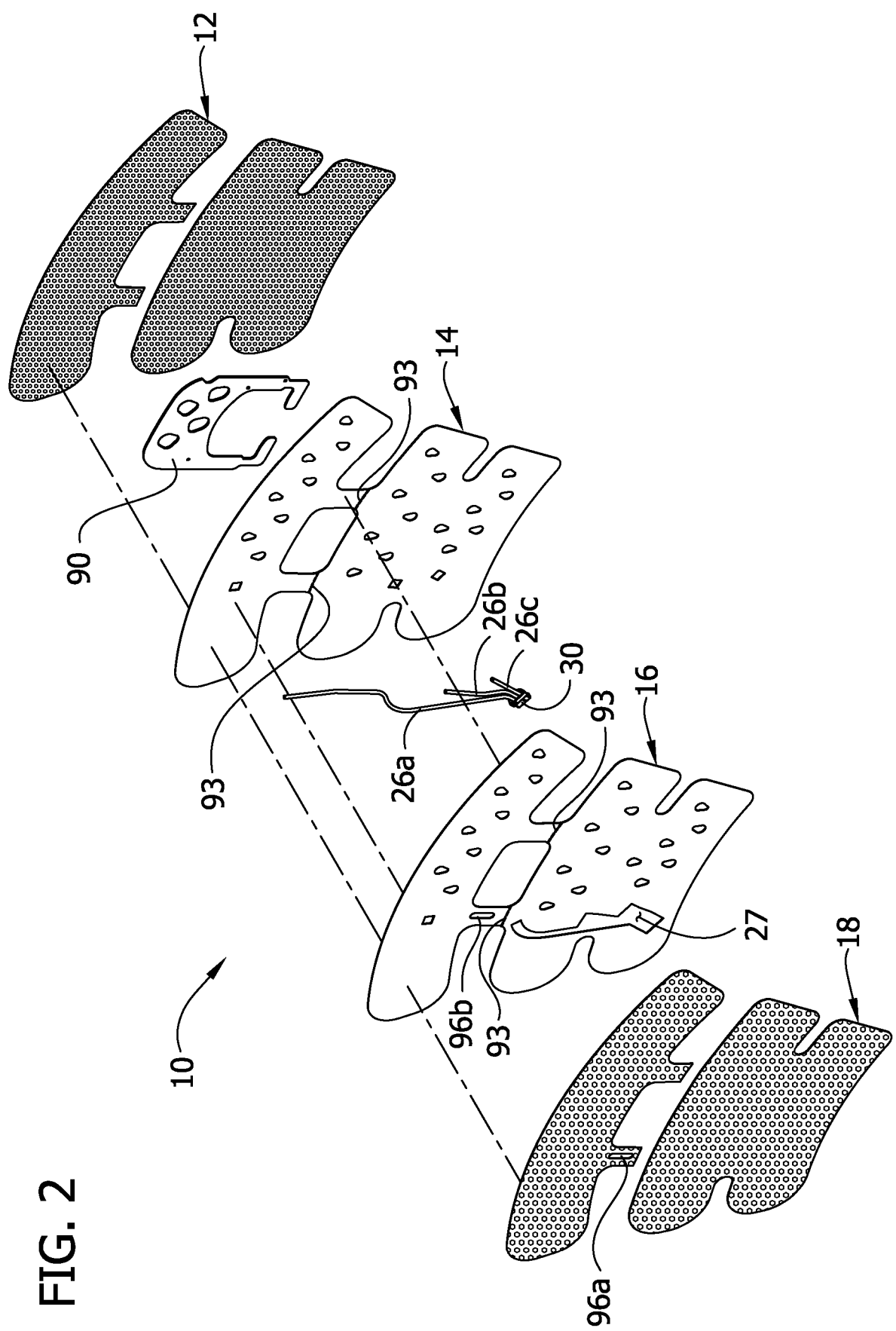

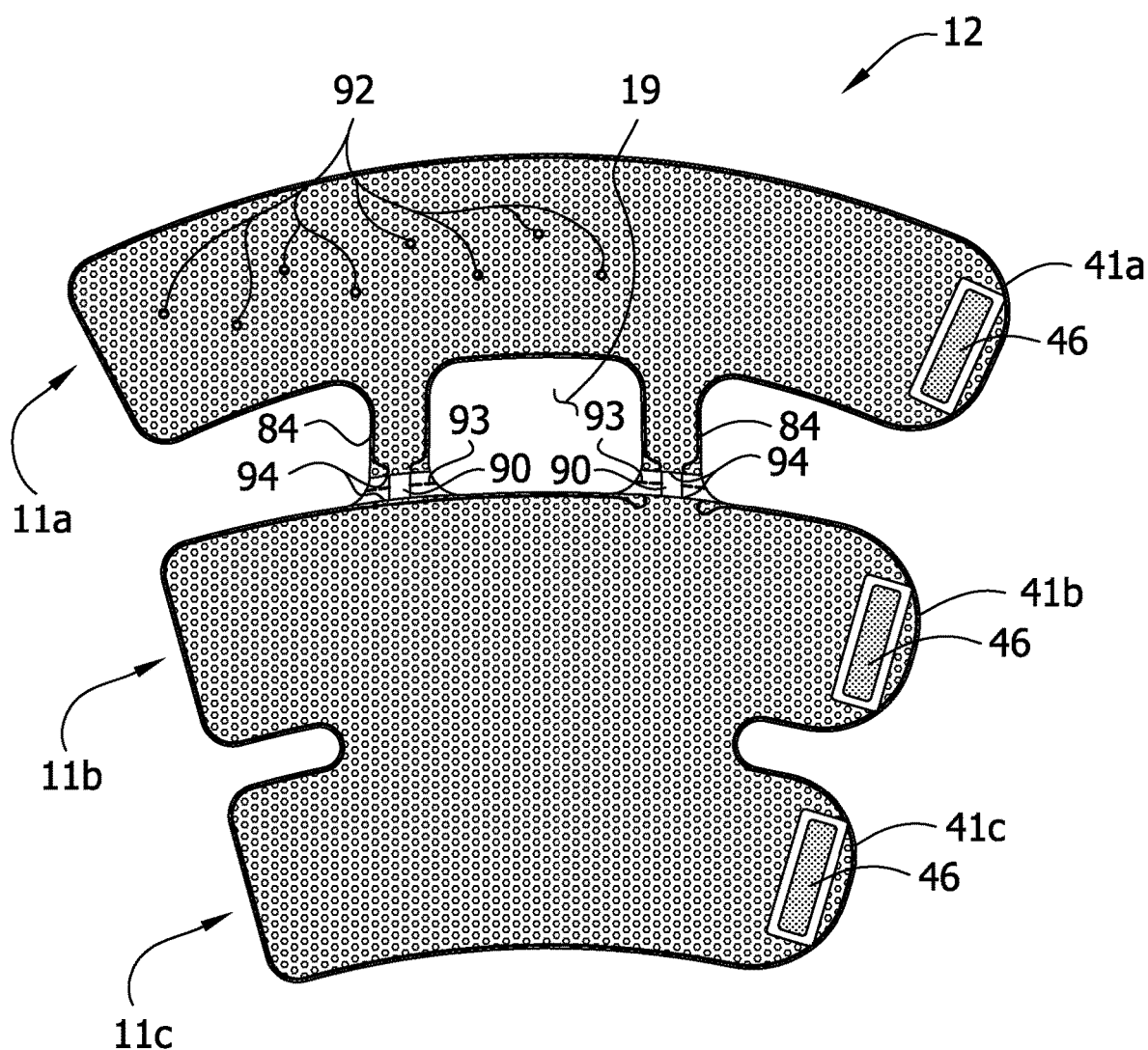

COMPRESSION SLEEVE WITH IMPROVED POSITION RETENTION

FIELD OF THE INVENTION

The present invention is directed generally to a compression device for applying compression therapy to a body part of a wearer, and more particularly to a compression device with an improved capability to retain its position on the body part.

BACKGROUND OF THE INVENTION

Compression garments for applying intermittent compression therapy to a body part (e.g., a limb such as a leg) have many applications, including deep vein thrombosis prophylaxis, edema prevention, and aiding in wound healing. It is sometimes desirable to provide active compression therapy during and after surgical procedures. The performance of these compression garments is sensitive to the ability of the garment to retain its initial fit and position around the body part. This can be very difficult when the patient moves, such as by walking, sitting, standing, and rolling over. The garments tend to loosen around the body part or slide down the body part causing misalignment of inflatable bladders on the garment with respect to the body part, which may result in ineffective compression therapy and/or discomfort. Thus, a compression garment needs to "stay up" in use.

SUMMARY OF THE INVENTION

In one aspect of the present invention a compression garment for applying compression to a part of a wearer's body generally comprises a layer of material sized and shaped for wrapping around the body part such that the layer of material encircles and conforms to the body part. A stay up device is operatively connected to the layer of material for supporting the layer of material against movement along a length of the body part. The stay up device includes a first region, a second region and at least one leg portion extending between and interconnecting the first and second regions. The second region being adapted to operatively engage a portion of the wearer's body adjacent to the second region for locating the stay up device relative to the wearer's body to support the layer of material in a generally fixed location relative to the body.

In another aspect of the present invention, a compression garment for applying compression to a part of a wearer's body generally comprises an inner layer and an outer layer in generally opposing relation with each other. The inner and outer layers define a thigh section, a calf section and a bridge section between the thigh and calf sections. The thigh section is sized and shaped for placement around a thigh of the wearer and the calf section is sized and shaped for placement around a calf of the wearer. Bladders are disposed between the inner and outer layers for applying pressure to the part of the wearer's body. At least one bladder is located in the thigh section and at least one bladder is located in the calf section. A stay up device is disposed between the inner and outer layers. The stay up device has a first region disposed at least partially in the thigh section of the garment, a second region disposed at least partially in the calf section of the garment and a leg portion extending between and interconnecting the first and second regions and disposed at least partially in the bridge section of the garment. The second region of the stay up device is adapted to engage a calf of the wearer to positively locate the stay up device for providing structural support to the thigh section of the garment.

Other objects and features will be in part apparent and in part pointed out hereinafter.

BRIEF DESCRIPTION OF THE DRAWINGS

FIG. 2 is an exploded perspective of the compression sleeve;

FIG. 3 is a rear elevation of the compression sleeve showing an inner layer;

Corresponding reference characters indicate corresponding parts throughout the drawings.

DESCRIPTION OF THE PREFERRED EMBODIMENTS

Figure 1:
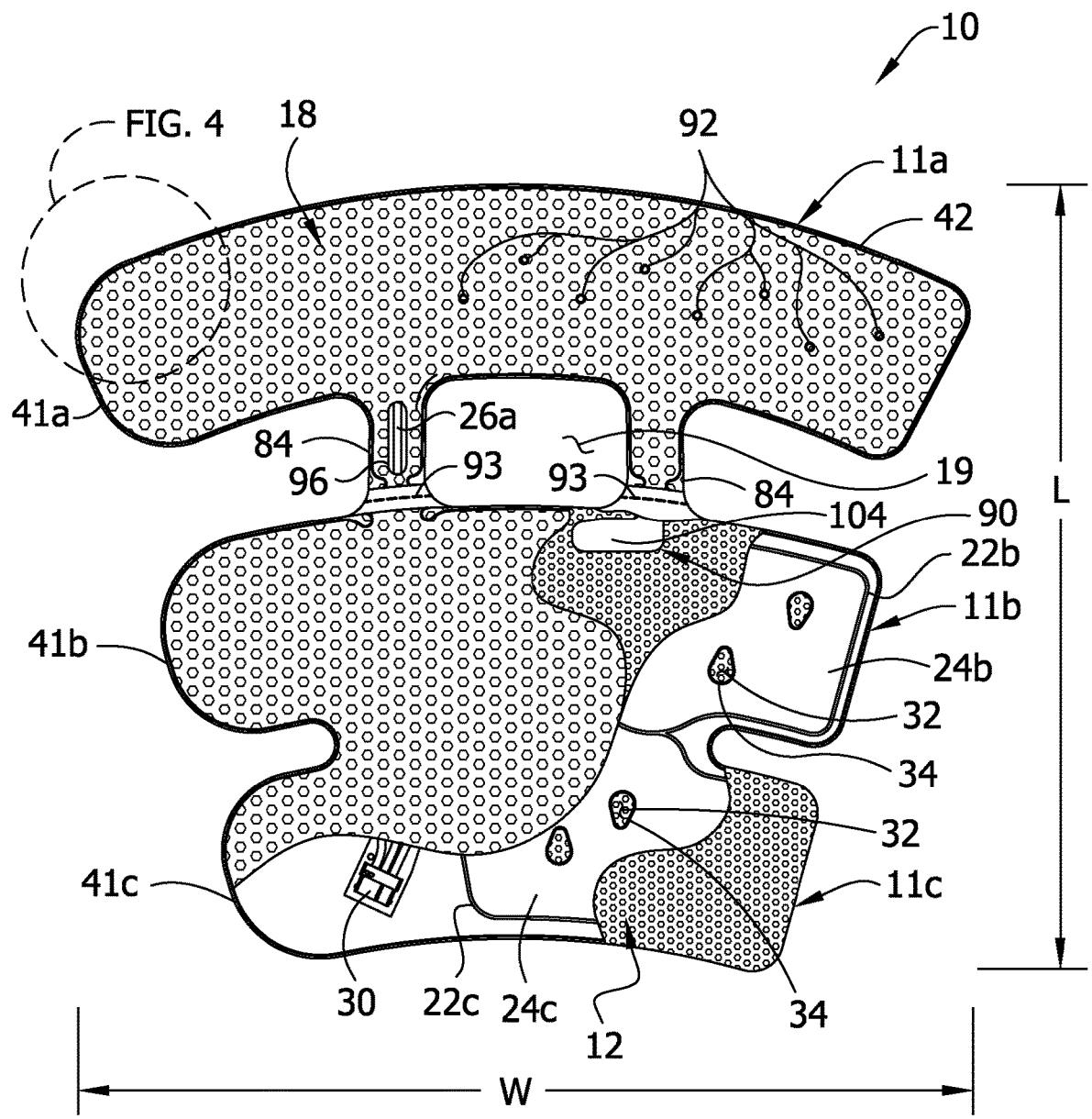
FIG. 1 is a front elevation of one embodiment of a compression sleeve with an outer cover and bladder layers of the sleeve partially removed to show underlying layers.
Figure 2A:
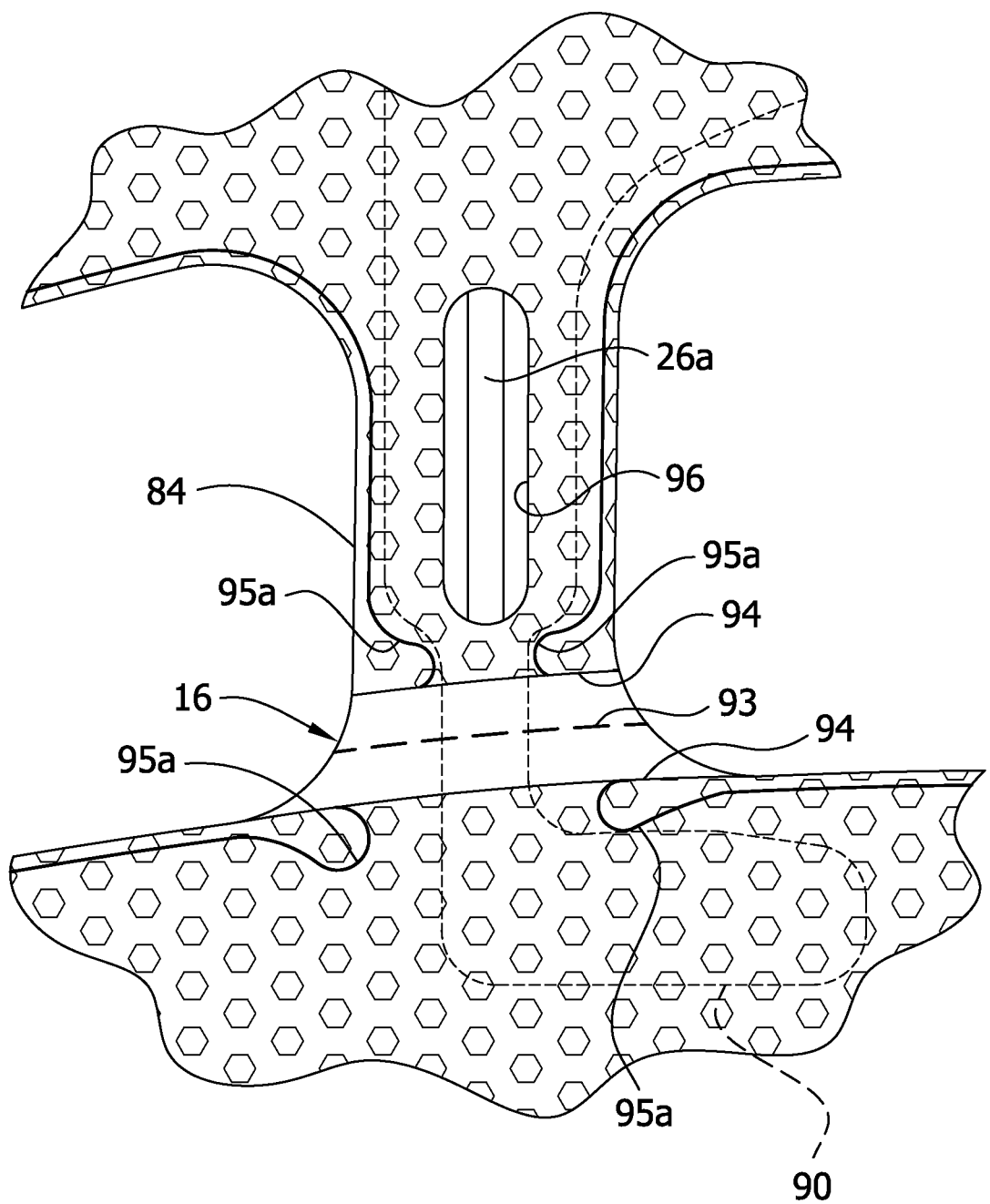
FIG. 2A is an enlarged, fragmentary view of FIG. 1 showing a perforation line extending across a left bridge of the compression sleeve.
Figure 2B:
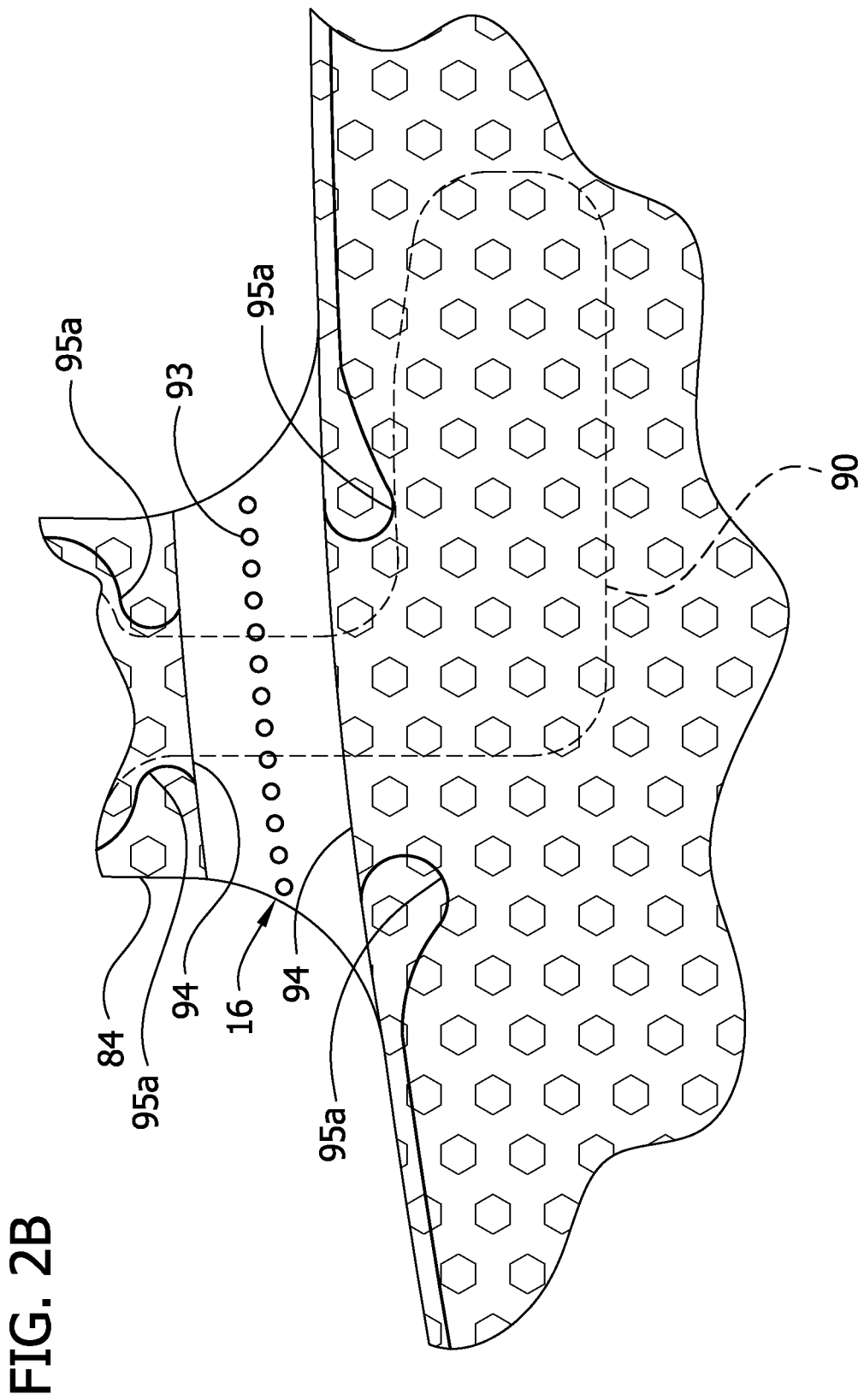
FIG. 2B is similar to FIG. 2A with the perforation line comprising circular openings.
Figure 2C:
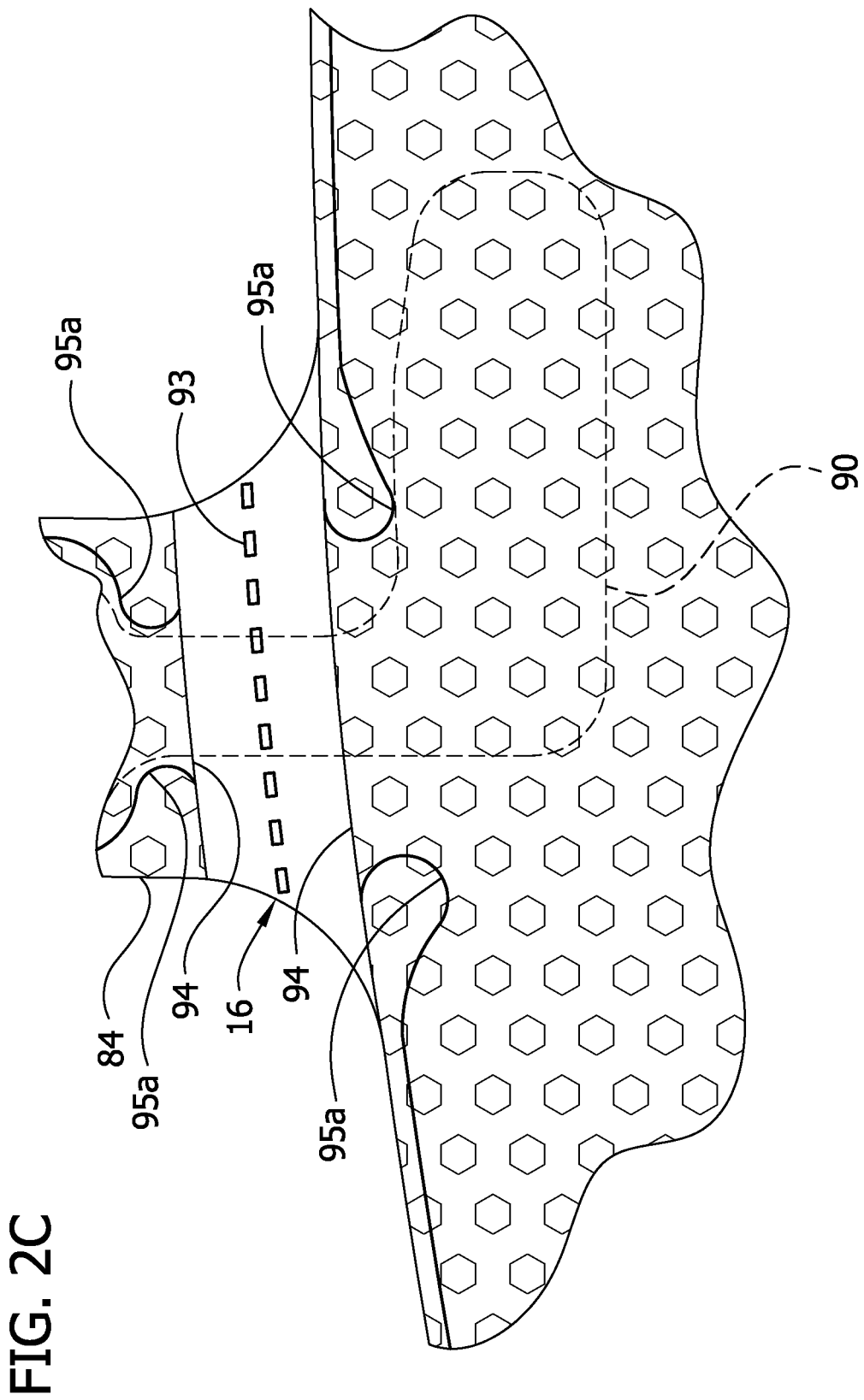
FIG. 2C is similar to FIG. 2A with the perforation line comprising slot-shaped openings.
Figure 2D:
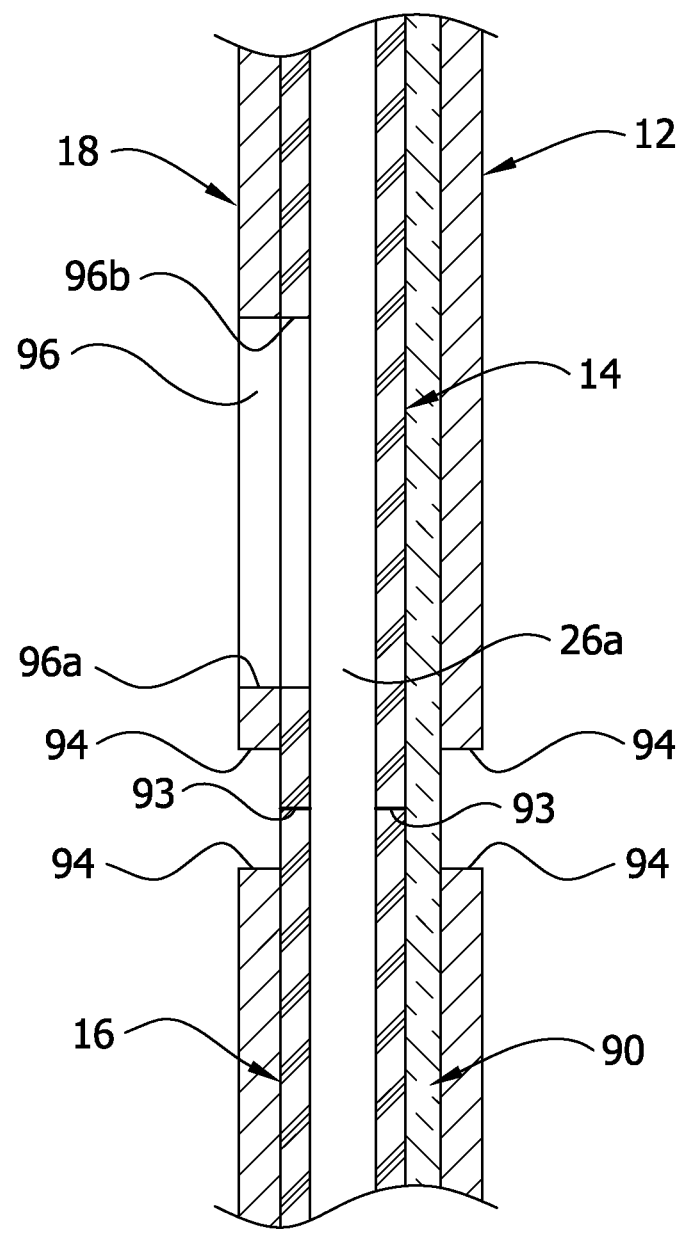
FIG. 2D is a section taken in the plane including line 2D-2D in FIG. 2A.

Referring now to the drawings, and in particular to FIGS. 1 and 2, one embodiment of a compression device (broadly, "a garment or a sleeve") for applying sequential compression therapy to a limb of a wearer is generally indicated at 10. The compression sleeve is of the type sized and shaped for being disposed around a leg of the wearer, but could be configured for application to other parts of the wearer's body. More specifically, the sleeve 10 has a width W (FIG. 1) for being wrapped around a full circumference of the leg and a length L (FIG. 1) for running from the ankle to a thigh of the leg. This type of sleeve is generally referred to in the art as a thigh-length sleeve including a thigh section 11a, a calf section 11b and an ankle section 11c. It is understood that other types of compression devices for being disposed about other limbs of the wearer's body are within the scope of the present invention.

Referring to FIGS. 1 and 2, the compression sleeve 10 comprises four layers secured together in the illustrated embodiment of the present invention. The scope of the present invention is not limited to four layers. More specifically, the compression sleeve comprises an inner layer, generally indicated at 12, on which a first intermediate layer (broadly, a first bladder layer), generally indicated at 14, is overlaid. A second intermediate layer (broadly, a second bladder layer), generally indicated at 16, overlies the first intermediate layer 14 and is secured thereto. An outer cover generally indicated at 18, overlies the second intermediate layer 16. In use, the inner layer 12 is disposed most adjacent to the limb of the wearer and is in contact with the limb of the wearer, and the outer cover 18 is most distant from the limb of the wearer. A knee opening 19 is formed through the sleeve 10 that is generally aligned with the back of the knee when the sleeve is applied to the leg. The layers have the same geometric shape and are superposed on each other so that edges of the layers generally coincide. The inner layer 12 and outer layer 18 may be secured to each other and/or to the intermediate layers 14, 16 in any suitable manner. It is contemplated that one or more of the layers 12, 14, 16, or 18 may not be superposed on a corresponding layer, but slightly offset to accommodate a particular feature of a patient's limb. Moreover, the number of sheets or thickness making up each layer 12, 14, 16, or 18 of the compression sleeve 10 may be other than described. The thickness of the layers may vary to add strength or to cause more expansion in one direction, such as toward the limb, during inflation.

Figure 5:
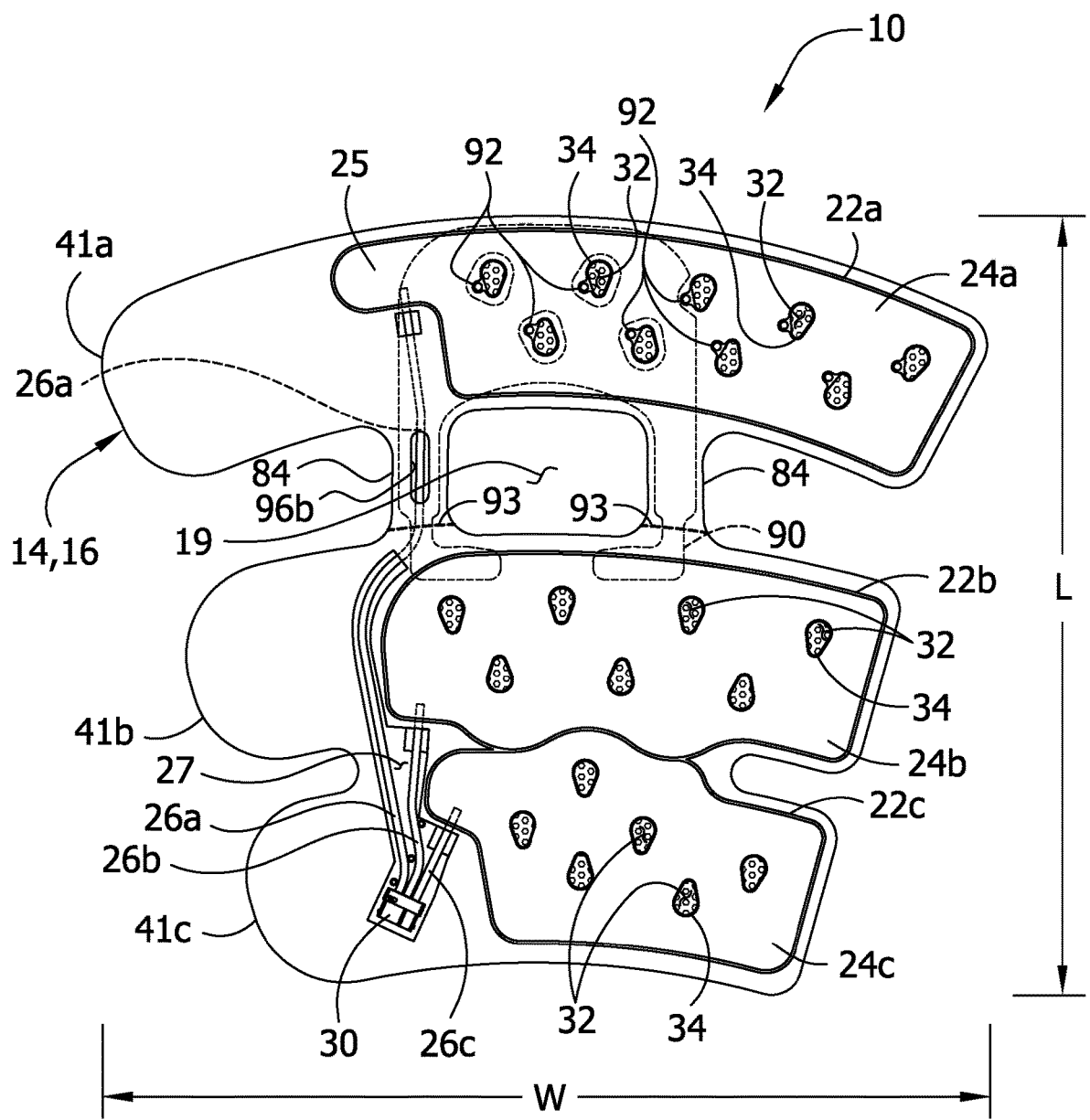
FIG. 5 is a front elevation of the compression sleeve with the outer cover removed.

Referring to FIGS. 1, 2 and 5, the first and second intermediate layers 14, 16, respectively, each include a single sheet of elastic material (broadly, "bladder material"). For example, the sheets 14 and 16 are made of a pliable PVC material as the bladder material. Layers 12 and 18 are made of a polyester material. The second intermediate layer 16 is secured to the first intermediate layer 14 via three separate bladder seam lines 22a, 22b, 22c defining a proximal bladder 24a, an intermediate bladder 24b and a distal bladder 24c, respectively, that are spaced apart longitudinally along the sleeve 10. The number of bladders may be other than three without departing from the scope of the present invention. As used herein, the terms "proximal", "distal", and "intermediate" represent relative locations of components, parts and the like of the compression sleeve when the sleeve is secured to the wearer's limb. As such, a "proximal" component or the like is disposed most adjacent to a point of attachment of the wearer's limb to the wearer's torso, a "distal" component is disposed most distant from the point of attachment, and an "intermediate" component is disposed generally anywhere between the proximal and distal components. Terms such as "proximal," "distal," "intermediate," "upper," "lower," "inner" and "outer" are used for convenience in describing relative locations but are not absolute requirements with respect to the environment as to the location of the various components.

For reasons discussed below, the proximal bladder 24a defines a proximal, lateral extension 25 near the upper edge margin of the sleeve 10 (see, FIG. 5). The bladders 24a, 24b, 24c are circumferential bladders meaning that they are sized and shaped to be wrapped around substantially the entire circumference of the wearer's limb or very nearly the entire circumference of the limb. For example, in one embodiment the bladders 24a, 24b, 24c each extend around at least 90% of a median circumference of a leg. It is to be understood that the circumferential extent may be other than described within the scope of the present invention The intermediate layers 14, 16 may be secured together by radiofrequency welding, adhesive, or other chemical and/or mechanical process. It is understood that the intermediate layers 14, 16 may be secured together at other locations, such as around their peripheries and at bladder seam lines 22a, 22b, 22c to further define the shape of the inflatable bladders 24a, 24b, 24c. For purposes discussed below, the first intermediate layer 14 is secured to the inner layer 12 along a seam line 42 (FIG. 1) that runs along the outer periphery of the first intermediate layer 14 so that central regions of the bladders 24a, 24b, 24c are not secured to the inner layer 12. This permits the bladders 24a, 24b, 24c to move relative to the inner layer 12. The second intermediate layer 16 may also be secured to the inner layer 12 along the same seam line 42. The first intermediate layer 14 may be secured to the inner layer 12 by RF welding or adhesive or in other suitable ways. This structure improves comfort as described below.

Figure 4:
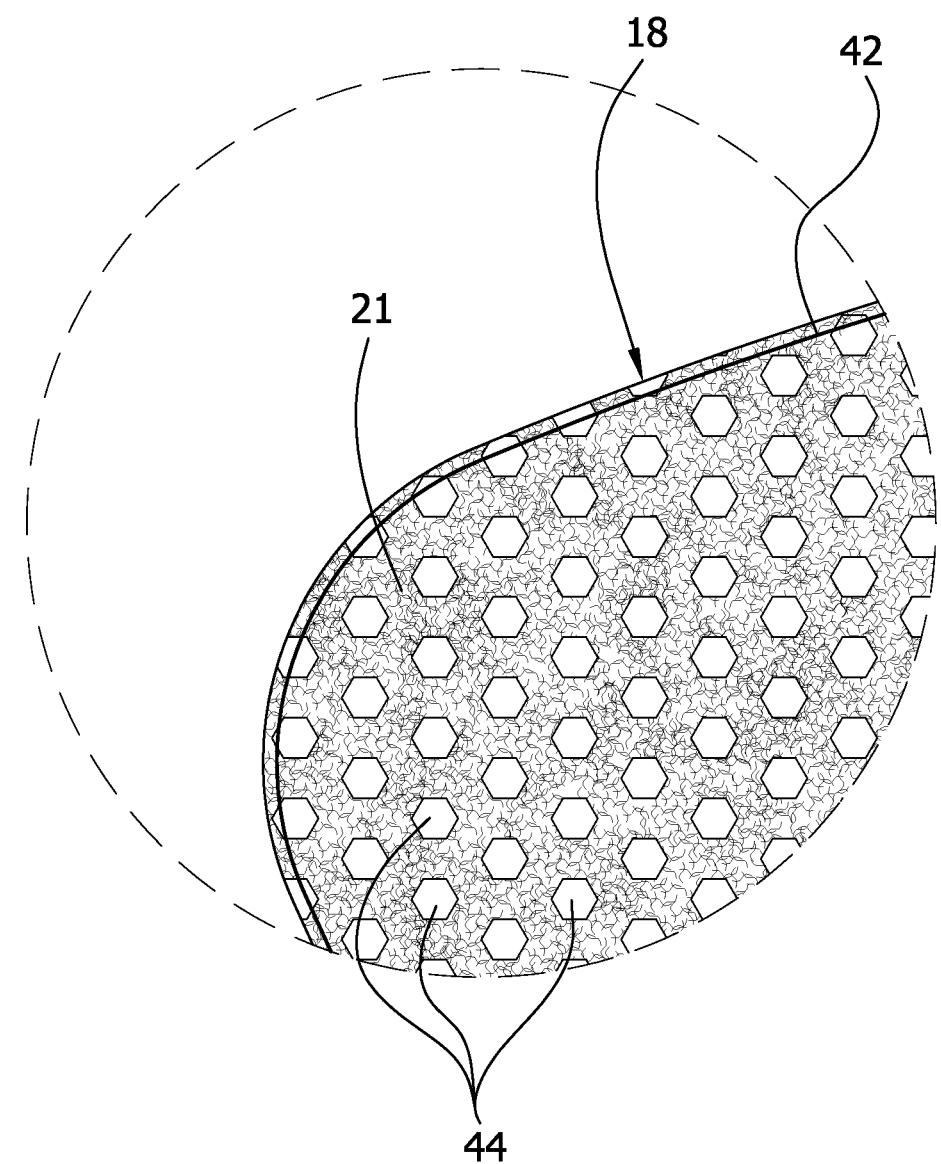
FIG. 4 is an enlarged fragmentary elevation of an outer cover of the sleeve illustrating loop material.

Referring to FIGS. 2 and 4, each inflatable bladder 24a, 24b, 24c receives fluid from a source of compressed fluid (not shown) via a dedicated proximal bladder tube 26a, intermediate bladder tube 26b, and distal bladder tube 26c, respectively, (FIG. 2). A tube line need not be dedicated to a bladder to practice the invention. Each tube 26a, 26b, 26c is disposed between the intermediate layers 14, 16 and secured to the respective bladder 24a, 24b, 24c by the respective bladder seam line 22a, 22b, 22c. As shown best in FIGS. 2 and 4, the first intermediate layer 16 defines a cutout 27 (FIG. 2) so that portions of the tubes 26a, 26b, 26c are not disposed between the intermediate layers. Other ways of securing the tubes 26a, 26b, and 26c to the bladders 24a, 24b, and 24c are within the scope of the invention. The opposite ends of the tubes 26a, 26b, 26c are grouped together using a second connector 30 (FIGS. 1 and 2) that is adapted to fluidly connect the tubes to the source of compressed fluid. The source of compressed fluid may be an air compressor under the control of a microprocessor that sequentially pressurizes the bladders as is generally known in the art. An exemplary air compressor is described in U.S. Pat. No. 5,876,359 to Bock, the disclosure of which is incorporated herein by reference. The bladders 24a, 24b, 24c may be configured to contain air pressurized to at least about 10 mm Hg (1333 Pa) to about 45 mm Hg (6000 Pa). The bladders should be capable of being repeatedly pressurized without failure. Materials suitable for the sheets include, but are not limited to, flexible PVC material that will not stretch substantially. In another embodiment, the intermediate layers may form a chamber for receiving an inflatable bladder that is formed separate from the chamber. In this embodiment, the layers need not be capable of containing pressurized air as along as the inflatable bladders are so capable. It will be noted that the bladders 24a, 24b, 24c can have openings 32 extending completely through the bladders, as described in the embodiments of the present invention.

Referring particularly to FIGS. 1 and 5, the sleeve 10 defines a connecting section including a pair of bridge members 84 on opposite sides of the knee opening 19 that extend between and connect a proximal portion of the sleeve that includes the proximal bladder 24a to the remainder of the sleeve. The proximal tube 26a generally lies along an axis of bridge member 84 to help provide structural, lengthwise support to the sleeve 10. As shown best in FIG. 4, the cutout 27 in the intermediate sheet 16 does not extend through the bridge member 84. As explained above, the proximal bladder tube 26a is secured to the proximal bladder 24a at the proximal, lateral extension 25. The proximal bladder tube 26a runs along a side of a distal portion of the proximal bladder 24a so that it does not enter the bladder until it reaches the proximal, lateral extension 25. The proximal bladder tube 26a may provide support to the thigh section 11a against bunching or sliding down the leg, but need not do so in the illustrated embodiments.

Referring to FIGS. 1, 3 and 5, the proximal bladder 24a is secured to the inner layer 12 and the outer cover 18 at spot welds 92 adjacent to the bladder openings 32 and within an outer perimeter of the bladder defined by the bladder seamline 22a. The spot welds 92 maintain the outer cover 18 and the inner layer 12 in proper position with respect to the bladders 24a, 24b, 24c. In other words, the spot welds 92 prevent the bladders 24a, 24b, 24c from substantially shifting relative to the inner layer 12 and the outer cover 18 while still providing the sleeve 10 with substantial flexibility. Too much movement of inner layer 12 and the outer cover 18 with respect to the bladders 24a, 24b, 24c may reduce the fit of the sleeve, thereby leading to reduced efficacy of the compression therapy. The proximal bladder 24a is free from securement to the inner layer 12 and outer cover 18 other than at the spot welds 92 to maintain flexibility of the sleeve so that mobility of the patient's leg is not compromised. Inner layer 12 may be joined to layer 16 at the spot welds 92 or the inner layer 12 may be joined at the seam line 34 of the opening 32. Away from the openings 32 and spot welds 92, the inner layer 12 is not joined to surface of the bladder material forming the bladder that expands to provide compression treatment to the patient's limb.

Referring to FIGS. 1 and 4, the entirety of an outer surface of the outer cover 18 also acts as a fastening component of a fastening system for securing the sleeve 10 to the limb of the wearer. In a particular embodiment, the outer cover 18 of mesh (FIG. 4), for example, has an outer surface comprising loops 44 that acts as a loop component of a hook-and-loop fastening system. A mesh construction, as shown in FIG. 4, has interconnected or weaved fibers 21 of material forming the outer cover 18. The loops 44 may be formed as part of the material of the outer cover 18 or otherwise disposed on the surface of the outer cover. A suitable material with such construction is a polyester mesh loop 2103 sold by Quanzhou Fulian Warp Knitting Industrial Co., Ltd. of Quanzhou City, China. Hook components 46 (FIG. 3) are attached to an inner surface of the inner layer 12 at the proximal, intermediate and distal flaps 41a, 41b, 41c, respectively. The loops 44 of the outer cover 18 allow the hook components 46 (FIG. 3) to be secured anywhere along the outer surface of the outer cover when the sleeve 10 is wrapped circumferentially around the limb of the wearer. This allows for sleeve 10 to be of a substantially one-size-fits-all configuration with respect to the circumferences of different wearers' limbs. Moreover, the outer cover 18 having the loops 44 allows the practitioner to quickly and confidently secure the sleeve 10 to the wearer's limb without needing to align the fastening components.

Figure 6:
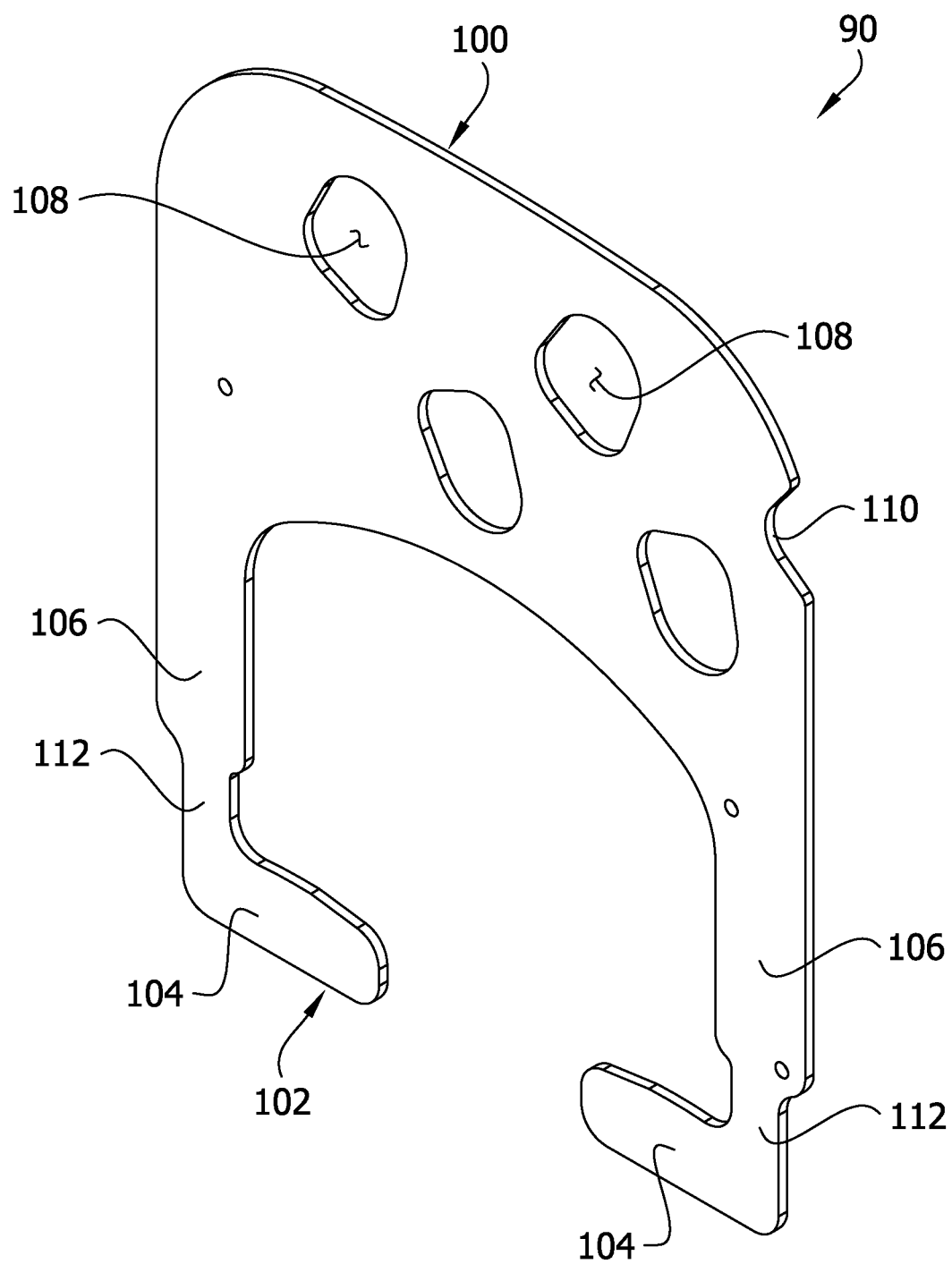
FIG. 6 is an enlarged perspective of a stay up insert of the compression sleeve.

Referring to FIGS. 2, 5 and 6, a stay up insert 90 (broadly, "a stay up device") is disposed between the first intermediate layer 14 and the inner layer 12. The insert 90 provides structural support to the sleeve 10 against buckling of the thigh section 11a in a vertical direction, and from sliding down the leg (e.g., as might otherwise be caused by buckling of the bridge members 84). The insert 90 comprises a first section 100, a second section 102 including first and second foot portions 104 and a bridge including first and second leg portions 106 connecting the first and second sections. The first section 100 is defined by a larger, roughly rectangular portion having rounded proximal corners. The first and second leg portions 104 each have a maximum width that is less than the width of either the first section 100 or the second section. Holes 108 in the first section 100 are generally aligned with the openings 32 in the proximal bladder 24a. An indent 110 in the first section 100 also provides clearance for an opening 32 in the proximal bladder 24a. The holes 108 and indent 110 are provided so that the insert 90 does not impede the evaporation function of the openings 32 in the intermediate layers 14, 16. Aligning the holes 108 with the openings 32 in the intermediate layers 14, 16 also fixes the insert 90 in place within the sleeve 10.

The leg portions 106 extend distally from the first section 100 and flank the knee opening 19. The bridge portions 106 include reduced width sections 112, the purpose of which will be explained hereinafter. The reduced width portions 112 have widths less than the maximum widths of the leg portions 106. The first and second foot portions 104 extend medially from the respective leg portion 106, below the knee opening 19. Free ends of the extension portions 104 are spaced apart. When the garment 10 is applied to the leg, the space overlies the popliteal vein. In this way, the insert 90 does not impede block flow of blood out of the leg through the popliteal vein. The insert 90 may be formed from pliable foam or any other suitable material for providing structural rigidity to the sleeve 10 to aid in keeping the sleeve in place on the limb of the wearer However, the foam is preferably also sufficiently pliable so that if in no way impedes wrapping the garment 10 around the leg.

Figure 7:
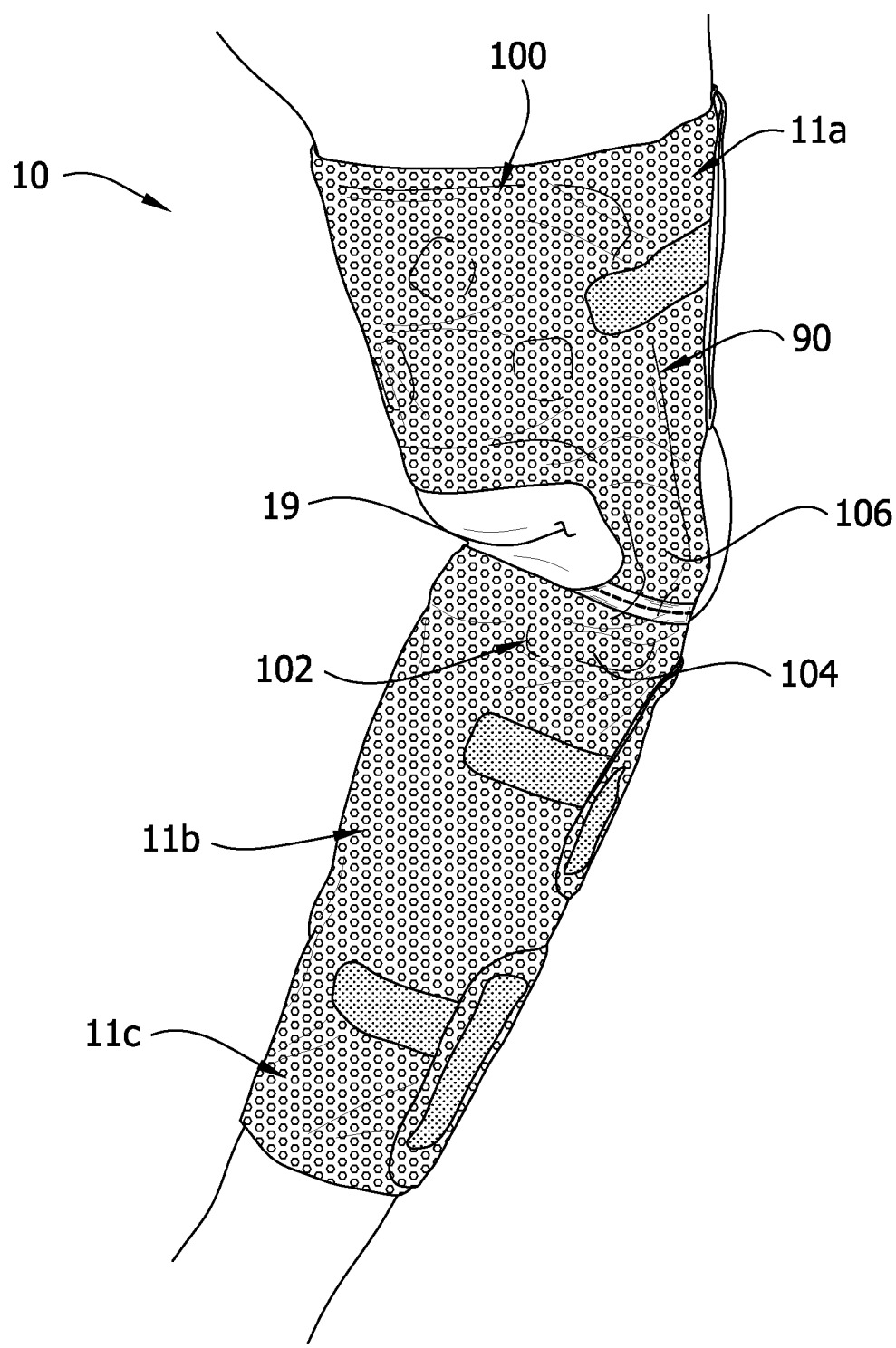
FIG. 7 is a perspective of the sleeve worn by a wearer illustrating interaction of the stay up insert with the wearer's leg.
Figure 8:
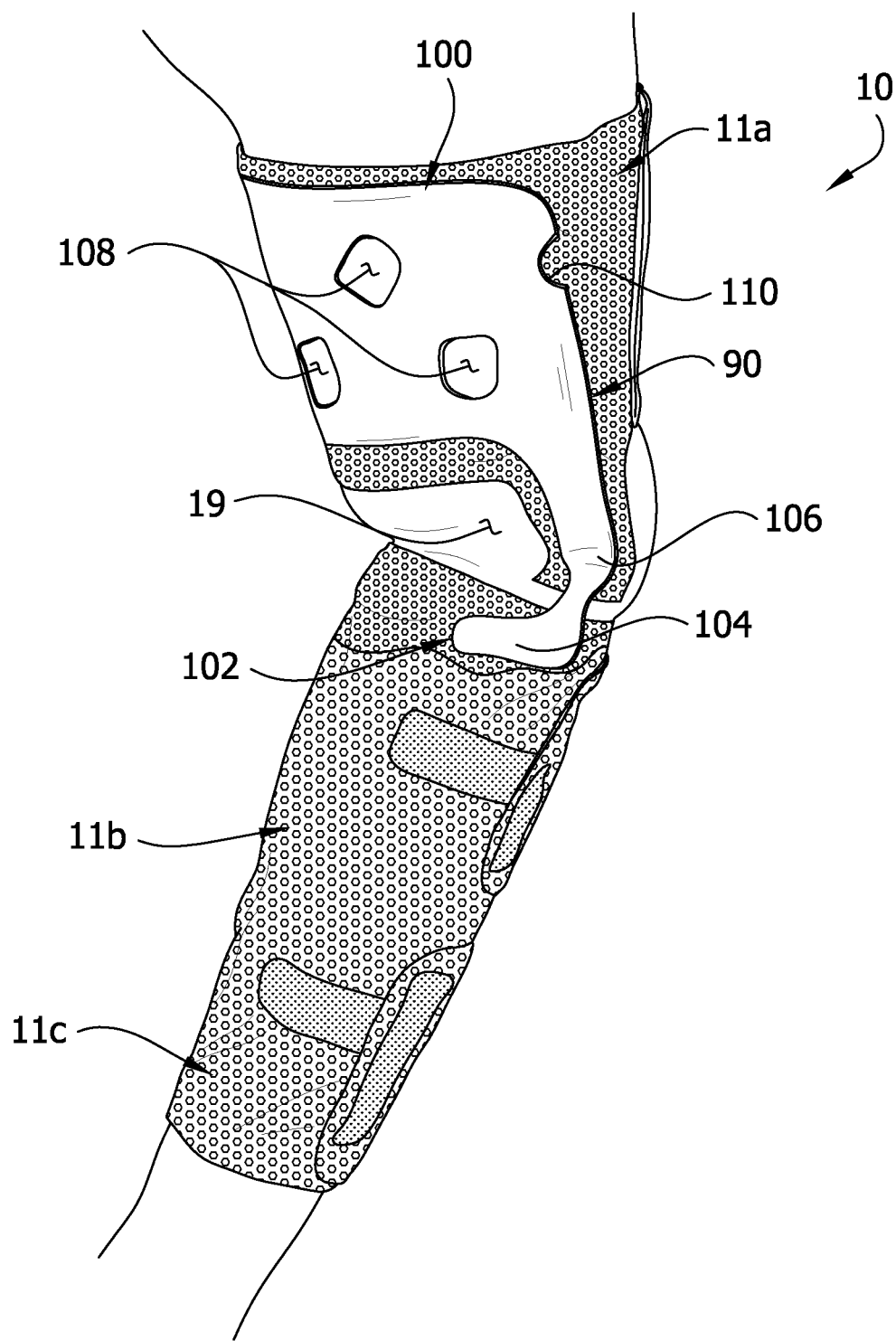
FIG. 8 is the perspective of FIG. 7 with portions of the sleeve partially removed to the stay up insert.

Referring to FIGS. 7 and 8, the first section 100 of the insert 90 extends substantially the entire height of thigh section 11a of the sleeve 10. In this manner, the insert 90 provides support to the thigh section 11a to resist against bunching (buckling) of the thigh section or the tendency of the thigh section to slide down the limb. The leg portions 106 of the insert 90 extend along the length of the bridge members 84 of the sleeve 10 providing structural rigidity to the bridge members of the sleeve. The foot portions 104 are configured to engage a calf of the wearer causing the calf to serve as a shelf for supporting the proximal portion (thigh section 11a and bridge members 84) of the sleeve 10. Also, upon flexion of the leg, the calf will exert an upward force on the foot portions 104 providing an additional supporting force to keep the sleeve 10 in its intended position on the leg.

Figure 9:
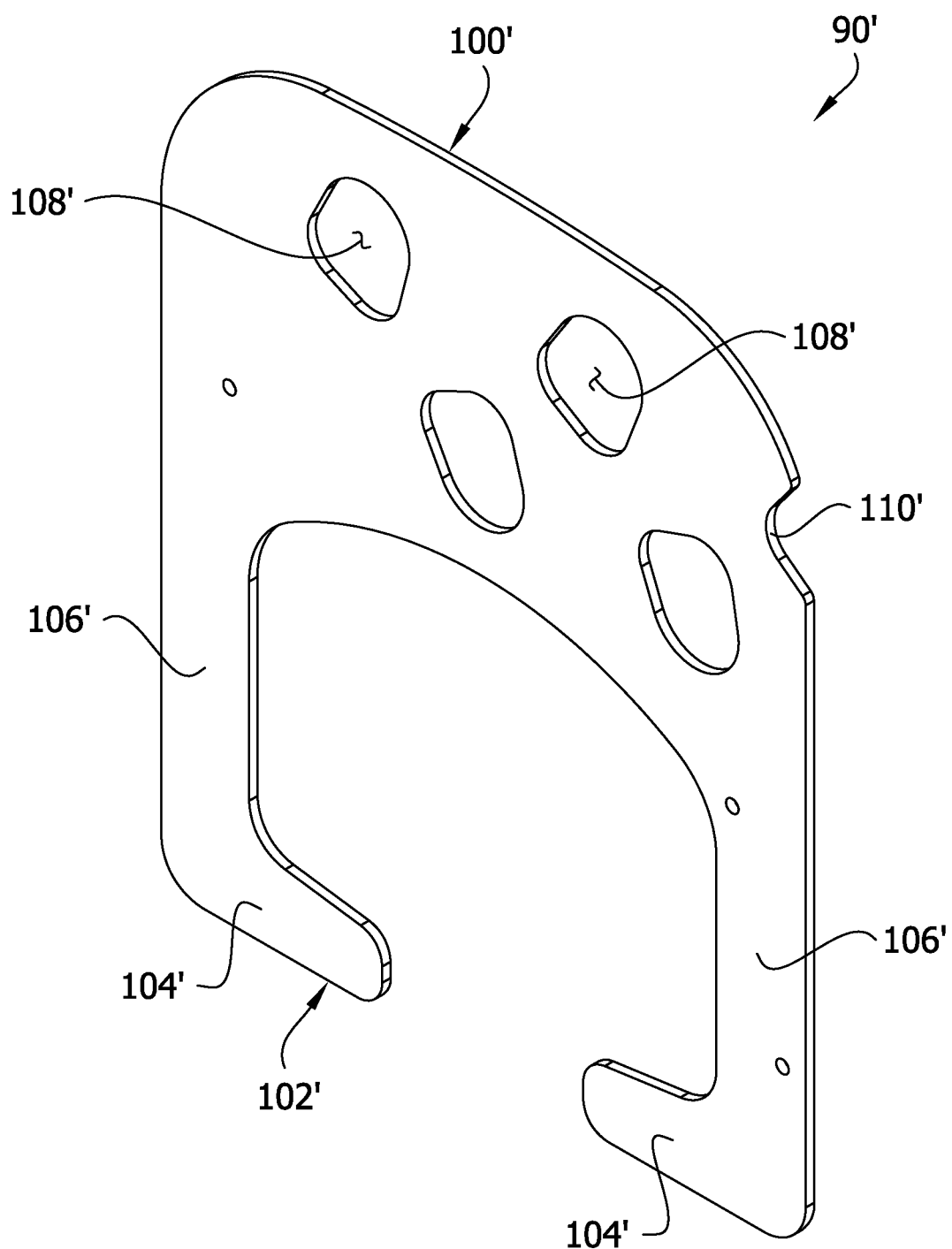
FIG. 9 is an enlarged perspective of a second embodiment of an insert of the compression sleeve.

In a second embodiment, an insert 90' (FIG. 9) comprises a bridge having leg portions 106' having no reduced width sections. The insert 90' otherwise functions substantially the same as insert 90. Thus, the same parts will be designated with the same reference numeral as in the prior embodiment, but with the addition of a prime after the numeral.

In the illustrated embodiment, the thigh section 11a is removable from the remainder of the sleeve 10 to convert the sleeve from thigh length to knee length. In particular, the proximal portion of the sleeve 10 that includes the proximal bladder 24a and the bridge members 84 are removable from the remainder of the sleeve. Tear lines comprising perforation lines 93 in the intermediate layers 14, 16, extend transversely across the intermediate layers adjacent to where the bridge members 84 join thigh section 11a to the calf and ankle sections 11b, 11c. In a preferred embodiment, the removal is destructive and permanent. It is understood that the sleeve may include one tear line or more than two tear lines within the scope of the invention. It is also understood that the shapes of the perforations may be circular (FIG. 2B) or slot-shaped (FIG. 2C) or other shapes within the scope of the invention. Other ways of weakening the sleeve 10 at the tear lines besides the perforation lines 93 are within the scope of the present invention. For example, the tear lines may include a thinned out portion of the intermediate layers 14, 16. It is also understood that the tear lines may be positioned to disconnect different ones of the sleeve sections (i.e., besides the thigh section 11a).

Neither the inner liner 12 nor the outer cover 18 have lines of weakness (e.g., perforations), although such a configuration is contemplated and within the scope of the present invention. Instead, as shown best in FIGS. 2A and 2D, both the inner liner 12 and the outer cover 18 are discontinuous generally adjacent to the perforation lines 93 in the intermediate layers 14, 16 so as to define respective opposing terminal edge margins 94 adjacent to the perforation lines. Each perforation line 93 is disposed between respective opposing terminal edge margins 94 of the inner liner 12 and the outer cover 18. In the illustrated embodiment, the terminal edge margins 94 of the inner liner 12 and the outer cover 18 are at least partially welded or otherwise secured to respective intermediate layers 14, 16 along terminal securement lines 95a associated with the respective left and right bridge members 84. The weld lines 95a are contiguous with the seamline 42 securing the bladder layers 14, 16 to the inner liner 12 and outer cover 18.

The terminal securement lines 95a on the bridge member 84 (FIGS. 2A-2C) are discontinuous and do not extend laterally across the bridge member. Instead, the terminal securement lines 95a converge toward each other and the center of the bridge 84. The terminal securement lines 95a, then turn back and curve down to the end of the terminal edge margins 94. On the left bridge member, the securement lines 95a define opposed inwardly projections on opposite sides of the bladder tube 26a and facilitate location of the bladder tube. However, the weld lines 95a do not permanently join the bladder tube 26a so that it can be removed, as described hereinafter. The reduced width sections 112 of the insert 90 are aligned with the terminal securement lines 95a where they converge and provide space for this convergence.

Generally, each terminal edge margin 94 is connected to the intermediate layers 14, 16 on a respective opposite side of the perforation line 93. By making the inner liner 12 and the outer cover 18 discontinuous at locations adjacent to the perforation lines 93 in the intermediate layers 14, 16, the sleeve is more easily torn at the perforation lines than if the inner liner and the outer cover were continuous and included perforation lines like the perforation lines in the intermediate layers. Moreover, the sleeve's resistance to tearing is greater at the terminal securement lines 95a. This greater tear resistance at the terminal securement lines 95a, facilitates more precise tearing of the sleeve along the perforation lines 93 and prevents incidental, significant deviation from the tear lines.

It is understood that the tear lines may be in other locations other than illustrated for removing the thigh section 11a from the remainder of the sleeve 10. As illustrated, the calf and ankle sections 11b, 11c do not have tear lines between them. It is also understood that the sleeve 10 may be configured to have other removable portions in addition to or instead of the thigh section 11a within the scope of the present invention.

As described previously, the proximal bladder tube 26a is disposed between the intermediate layers 14, 16 and extends through one of the bridge members 84. The proximal bladder tube 26a is releasably secured to the connector 30 so that the proximal bladder tube can be disconnected from the connector and so that the thigh section 11a can be removed from the remainder of the sleeve 10. The connector 30 and the proximal bladder tube 26a may be of the type disclosed in pending U.S. patent application Ser. No. 10/784,607, filed Feb. 23, 2004 and assigned to the assignee of the present application, the entirety of which is herein incorporated by reference. In particular, the connector 30 permits non-destructive disconnection of the proximal bladder tube 26a in preparation for removing the thigh section 11a. Because the proximal bladder tube 26a and leg portions 106 of the insert 90 extend through the bridge members 84 generally transverse to the tear line, it may be difficult to tear the sleeve 10 along the corresponding perforation lines in the intermediate layers 14, 16. Accordingly, a tube access opening or window 96 is formed by an opening 96a in the outer cover 18 and an aligned opening 96b in the second intermediate layer 16. Because the window extends through the outer cover 18 and the second intermediate layer 16 adjacent to the outer cover to expose a portion of the proximal bladder tube to facilitate removal of the proximal bladder tube 26a from the bridge member 84 before tearing the sleeve 10. In the illustrated embodiment, the tube access window 96 is generally oblong and extends less than the full axial length of one of the bridge members 84.

In use, the proximal bladder tube 26a can be disconnected from the connector 30 and then pulled through the tube access window 96 so that the tube no longer extends past the tear line between the intermediate layers 14, 16. With the tube 26a removed from between the intermediate layers 14, 16 at the corresponding tear line, the sleeve can be easily torn along the perforation lines 93 to remove the proximal portion, including the proximal bladder 24a, and the bridge members 84.

Similarly, as shown in the first embodiment of the insert 90, the leg portions 106 have the reduced width section 112 which makes it easier to pull the leg portions 106 and foot portions 104 from the knee section 11b of the sleeve 10. In addition to accommodating the terminal securement lines 95a, the reduced width portion 112 reduces the amount of material of the insert 90 at and below the bridge members 84. This construction makes it easier to remove the leg portions 106 and foot portions 104, from the knee section 11b of the sleeve 10. Thus, if the thigh section 11a and bridge members 84 are removed from the garment 10, the perforations 93 (see, FIG. 2a) are torn part way. The reduced width section 12 and extensions 104 are pulled out from the calf section 11b, and tearing of the perforation 93 is completed to separate the thigh section 11a and bridge members 84 from the remainder of the garment 10. Other ways of achieving separation are contemplated. For example, the leg portions of an insert (not shown) may have lines of weakness (e.g., perforations) that generally align with the perforations 93. In that instance, the extensions and part of the reduced width sections would be torn away from the remainder of the insert.

Having described the invention in detail, it will be apparent that modifications and variations are possible without departing from the scope of the invention defined in the appended claims.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above constructions without departing from the scope of the invention, it is intended that all matter contained in the above description and shown in the accompanying drawings shall be interpreted as illustrative and not in a limiting sense.

What is claimed is:

1. A compression garment for applying compression to a wearer's leg, the garment comprising:

a layer of material sized and shaped for wrapping around the wearer's leg such that the layer of material encircles and conforms to the wearer's leg;

an asymmetrical stay up device operatively connected to the layer of material for supporting the layer of material against movement along a length of the wearer's leg, the stay up device including a first region, a second region and at least one leg extending between and interconnecting the first and second regions, the second region being positioned on the layer of material to operatively engage a back of the wearer's leg when the compression garment is properly worn to exert an upward force on the second region providing an additional supporting force for locating the stay up device relative to the wearer's leg to support the layer of material in a generally fixed location relative to the wearer's leg;

wherein the layer of material comprises an upper section, a lower section and a bridge section between the upper and lower sections, at least one bladder being disposed in the upper section, the first region of the stay up device is at least partially disposed at the upper section, and the second region of the stay up device is at least partially disposed at the lower section;

the stay up device comprising a pliable foam material of greater structural rigidity than the layer of material to hold the upper section of the layer of material against sliding down the wearer's leg, the layer of material defining an opening positioned for registration with a knee of the wearer, the second region comprising a foot projecting in a generally lateral direction of the garment from the leg beneath a distal-most edge of the knee opening such that a line perpendicular to the distal-most edge and intersecting the distal-most edge intersects a portion of the foot.

2. A compression garment as set forth in claim 1 wherein the stay up device is non-inflatable and formed separately from the layer of material.

3. A compression garment as set forth in claim 2 wherein the leg comprises a first leg, the stay up device further comprising a second leg spaced from the first leg and extending from the first region of the stay up device to the second region of the stay up device.

4. A compression garment as set forth in claim 3 wherein the foot of the second region comprises a first foot, the second region further comprising a second foot projecting in a generally lateral direction of the garment from the second leg.

5. A compression garment as set forth in claim 4 wherein the first and second feet project toward each other and are separated from each other by a space.

6. A compression garment as set forth in claim 5 wherein the first and second legs each have respective maximum widths, the maximum widths of the legs being less than a width of the second region and less than a width of the first region.

7. A compression garment as set forth in claim 6 wherein the first and second legs each have respective reduced width sections connected to the feet, the reduced width sections each having a width less than the maximum width of the respective first and second legs.

8. A compression garment as set forth in claim 7 wherein the first and second legs of the stay up device are at least partially disposed at the bridge section.

9. A compression garment as set forth in claim 8 wherein the reduced width section of each of the first and second legs is disposed at a junction between the bridge section and the lower section.

10. A compression garment as set forth in claim 9 wherein the bridge section is releasably attached to the lower section.

11. A compression garment as set forth in claim 10 further comprising perforations extending across the junction between the bridge section and the lower section.

12. A compression garment as set forth in claim 8 wherein the upper section is sized and shaped for placement around a thigh of the wearer and the lower section is sized and shaped for placement around a calf of the wearer.

13. A compression garment as set forth in claim 8 wherein the upper section of the layer of material has a height and the first region of the stay up device extends substantially along the entire height of the upper section.

14. A compression garment as set forth in claim 1 wherein the second region of the stay up device operatively engages a wearer's calf when the layer of material is wrapped around a wearer's leg.

15. A compression garment as set forth in claim 1 wherein the at least one bladder defines at least one opening extending through the at least one bladder, the stay up device defining a least one hole in the first region, the at least one hole generally aligned with the at least one opening defined by the at least one bladder.

16. A compression garment for applying compression to a part of a wearer's body, the garment comprising:

an inner layer and an outer layer in generally opposing relation with each other, the inner and outer layers defining a thigh section, a calf section and a bridge section between the thigh and calf sections, the thigh section being sized and shaped for placement around a thigh of the wearer and the calf section being sized and shaped for placement around a calf of the wearer;

bladders disposed between the inner and outer layers for applying pressure to the part of the wearer's body, at least one bladder being located in the thigh section and at least one bladder being located in the calf section; and an asymmetrical stay up device disposed between the inner and outer layers, the stay up device having a first region disposed at least partially in the thigh section of the garment, a second region disposed at least partially in the calf section of the garment and a leg extending between and interconnecting the first and second regions and disposed at least partially in the bridge section of the garment, the second region of the stay up device overlapping at least a portion of the at least one bladder in the calf section to engage a calf of the wearer when the compression garment is properly worn to exert an upward force on the second region providing an additional supporting force to positively locate the stay up device in the thigh section of the garment for providing structural support to the thigh section of the garment and to hold the thigh section of the garment in place around the thigh of the wearer, the stay up device comprising a pliable foam material having a greater structural rigidity than the inner layer and the outer layer to hold the thigh section against sliding down the wearer's leg.

17. A compression garment as set forth in claim 16 wherein the stay up device is non-inflatable and formed separately from the bladders, the leg of the stay up device comprising a first leg, the stay up device further comprising a second leg spaced from the first leg along the first region and extending from the first region of the stay up device to the second region of the stay up device, and wherein the second region comprises first and second feet projecting in a generally lateral direction of the garment from respective ones of the first and second legs toward the other one of the first and second legs.

18. A compression garment as set forth in claim 17 wherein the inner and outer layers define an opening positioned for registration with a knee of the wearer, the bridge section comprising bridge members extending along opposite sides of the knee opening, each of the first and second feet projecting in a lateral direction of the garment from the respective leg beneath a distal-most edge of the knee opening such that a portion of each foot and a corresponding portion of the distal-most edge of the knee opening are disposed on respective common longitudinal axes.

19. A compression garment as set forth in claim 16 wherein the thigh section has a height and the first region of the stay up device extends substantially along the entire height of the thigh section.

20. A compression garment as set forth in claim 16 wherein the inner and outer layers further define an ankle section below the calf section, at least one of the bladders being located in the ankle section.

21. A compression garment as set forth in claim 16 wherein the at least one bladder in the thigh section defines at least one opening extending through the at least one bladder in the thigh section, the stay up device defining at least one hole in the first region, the at least one hole generally aligned with the at least one opening defined by the at least one bladder in the thigh section.

22. A compression garment for applying compression to a leg of a wearer's body, the garment comprising:
   a layer of material sized and shaped for wrapping around the wearer's leg such that the layer of material encircles and conforms to the wearer's leg wherein the layer of material includes an inner layer and an outer layer of material;
   a bladder disposed between the inner and outer layers for applying pressure to at least a portion of the wearers leg;
   an asymmetrical stay up device operatively connected to the layer of material for supporting the layer of material against movement along a length of the wearer's leg, the stay up device including a first region, a second region, a first leg extending between and interconnecting the first and second regions, and a second leg extending between and interconnecting the first and second regions, the second region being positioned on the layer of material to operatively engage a portion of the wearer's leg adjacent to the second region for locating the stay up device relative to the wearer's body to support the layer of material in a generally fixed location relative to the body;
   wherein the layer of material comprises an upper section, a lower section, a bridge section between the upper and lower sections, and an opening positioned for registration with the knee of the wearer; the first region of the stay up device being at least partially disposed at the upper section and the second region being at least partially disposed in the lower section, wherein
   the stay up device has a construction and shape to hold the upper section of the layer of material against sliding down the wearer's leg;
   wherein the second region of the stay up device comprises a first foot projecting in a generally lateral direction of the garment from the first leg beneath a distal-most edge of the knee opening when the layer of material is wrapped around the wearer's leg, and a second foot projecting in a generally lateral direction of the garment from the second leg, the first and second feet project toward each other and are separated from each other by a space.

23. The compression device as set forth in claim 22, wherein the stay up device comprises a pliable foam material having greater structural rigidity than the layer of material.

* * * * *